United States Patent
Honma et al.

[19]

[11] Patent Number: 6,083,974
[45] Date of Patent: Jul. 4, 2000

[54] BENZOTHIOPHENECARBOXAMIDE DERIVATIVES AND PGD$_2$ ANTAGONISTS COMPRISING THEM

[75] Inventors: Tsunetoshi Honma, Nara; Yoshiharu Hiramatsu; Akinori Arimura, both of Osaka, all of Japan

[73] Assignee: Shionogi & Co., Ltd., Osaka, Japan

[21] Appl. No.: 09/308,176

[22] PCT Filed: Dec. 10, 1997

[86] PCT No.: PCT/JP97/04527

§ 371 Date: May 17, 1999

§ 102(e) Date: May 17, 1999

[87] PCT Pub. No.: WO98/25919

PCT Pub. Date: Jun. 18, 1998

[30] Foreign Application Priority Data

Dec. 13, 1996 [JP] Japan .................. 8-333495
Sep. 19, 1997 [JP] Japan .................. 9-254001

[51] Int. Cl.[7] .................. A61K 31/38; C07D 333/56; C07D 333/52
[52] U.S. Cl. .................. 514/443; 549/58; 549/51
[58] Field of Search .................. 549/58, 51; 514/443

[56] References Cited

U.S. PATENT DOCUMENTS

| | | | |
|---|---|---|---|
| 5,356,926 | 10/1994 | Boschelli et al. .................. | 514/445 |
| 5,712,304 | 1/1998 | Elbe et al. .................. | 549/53 |
| 5,792,763 | 8/1998 | Fritz et al. .................. | 514/443 |
| 5,863,936 | 1/1999 | Gaete et al. .................. | 514/443 |

FOREIGN PATENT DOCUMENTS

| | | |
|---|---|---|
| 0 171 145 | 2/1986 | European Pat. Off. . |
| 0 226 346 | 6/1987 | European Pat. Off. . |
| 0 290 285 | 11/1988 | European Pat. Off. . |
| 0 837 052 | 4/1998 | European Pat. Off. . |

OTHER PUBLICATIONS

Seno, K., et al., "Thromboxane A$_2$ Receptor Antagonist. III. Synthesis and Pharmacological Activity methylbicyclo [3.1.1]heptane Derivatives with a Substituted Sulfonylamino Group at C–2," Chem. Pharm. Bull., vol. 37, No. 6, pp. 1524–1533 (1989).

Martin–Smith, M., et al., "Benzo[b]thiophen Derivatives. Part VI. The Synthesis of a 3–(2–Amino–ethyl)–5–hydroxybenzol[$_b$]thiophen and Related Compounds," J. Chem. Soc., Section C, pp. 1899–1905 (1967).

Tsuri, T., et al., "Bicyclo[2.2.1]heptane and 6,6–Dimethylbicyclo[3.1.1]heptane Derivatives: Orally Active, Potent, and Selective Prostaglandin D2 Receptor Antagonists," J. Med. Chem., vol. 40, pp. 3504–3507 (1997).

*Primary Examiner*—Deborah C. Lambkin
*Attorney, Agent, or Firm*—Foley & Lardner

[57] ABSTRACT

A compound, a pharmaceutically acceptable salt thereof, or a hydrate thereof having PGD$_2$-antagonistic activities, inhibitory activities against infiltration of eosinophils, and being useful as a drug for treating diseases, such as systemic mastocytosis and disorder of systemic mast cell activation, as well as tracheal contraction, asthma, allergic rhinitis, allergic conjunctivitis, urticaria, ischemic reperfusion injury, inflammation and atopic dermatitis, which is shown by the following formula (I):

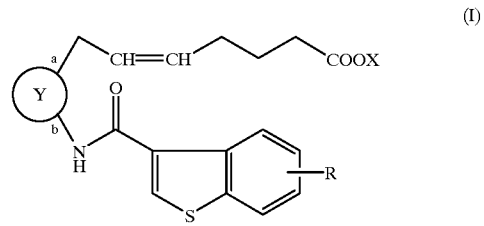

(I)

is provided

26 Claims, 1 Drawing Sheet

BENZOTHIOPHENECARBOXAMIDE DERIVATIVES AND PGD₂ ANTAGONISTS COMPRISING THEM

This application is a 371 of PCT/JP97/04527 Dec. 10, 1997.

FIELD OF THE INVENTION

The present invention relates to benzothiophenecarboxamide derivatives, the intermediates therefor, pharmaceutical compositions comprising them, $PGD_2$ (prostaglandin $D_2$) antagonists comprising them, and drugs for treating nasal blockage comprising them.

BACKGROUND OF THE INVENTION

Some of bicyclic amide derivatives analogues to the compounds of the present invention have been described that they are useful as thromboxane $A_2$ ($TXA_2$) antagonists (Japanese Patent Publication (Kokoku) No. 53295/1991). However, in the Japanese Patent Publication (Kokoku) No. 53295/1991, it has only been described that the compounds are useful as $TXA_2$ antagonists, but there is no suggestion of the useful thereof as $PGD_2$ antagonists as found in the present invention. On the other hand, in Japanese Patent Publication (Kokoku) No.79060/1993, Japanese Patent Publication (Kokoku) No.23170/1994 and Chem. Pharm. Bull. Vol.37, No.6 1524–1533 (1989), it has been described bicyclic amide derivatives, which are intermediates for bicyclic sulfonamide derivatives. However, the compounds disclosed therein are different from those of the present invention in the species of substituents at the amide portion. And some of the compounds analogues to the compounds of the present invention has been described that they are useful as $PGD_2$ antagonists in WO 97/00853. However, there is no suggestion that the compounds disclosed in WO 97/00853 possess a inhibitory activity against infiltration of eosionophils.

$TXA_2$ has been known to have various activities such as platelet aggregation, thrombogenesis, etc. The $TXA_2$ antagonists have therefore been considered to be useful as anti-thrombotic agents as well as drugs in the treatment of myocardial infarction or asthma.

On the other hand, the $PGD_2$ antagonists of the present invention are useful in the improvement of conditions due to excessive production of $PGD_2$, particularly as drugs for treating diseases in which mast cell dysfunction is involved, for example, systemic mastocytosis and disorder of systemic mast cell activation as well as for tracheal contraction, asthma, allergic rhinitis, allergic conjunctivitis, urticaria, ischemic reperfusion injury, inflammation, and atopic dermatitis.

$PGD_2$ is a major prostanoid that is produced in and released from mast cells in which it is produced through $PGG_2$ and $PGH_2$ from arachidonic acid by the action of cyclooxygenase activated by immunological or unimmunological stimulation. $PGD_2$ has various potent physiological and pathological activities. For example, $PGD_2$ can cause strong tracheal contraction to lead to bronchial asthma, and in a systemic allergic state, it dilates the peripheral vessels to cause an anaphylactic shock. Especially, much attention has been paid to the theory that $PGD_2$ is one of the casual substances responsible to the onset of nasal blockage in the allergic rhinitis. Therefore, it has been proposed to develop an inhibitor against the biosynthesis of $PGD_2$ or an antagonist of $PGD_2$ receptor as a drug for the reduction of nasal blockage. However, the inhibitor of $PGD_2$ biosynthesis possibly much affects the synthesis of prostaglandins in other parts of organisms, and therefore, it is desirable to develop an antagonist (blocker) specific to the $PGD_2$ receptor.

DISCLOSURE OF THE INVENTION

The present inventors have studied intensively to develop $PGD_2$ receptor antagonists (blockers) specific to the $PGD_2$ receptor, and found that a series of compounds of the formula (I) below, pharmaceutically acceptable salts thereof, or hydrates thereof possess a potent activity as $PGD_2$ receptor antagonists and a inhibitory activity against infiltration of eosionophils, and are useful as drugs for treating nasal blockage. The compounds of the present invention having $PGD_2$ antagonist activity are different from the known $TXA_2$ antagonists in the active site and mechanism, application, and character.

Accordingly, the present invention provides a compound of the formula (I):

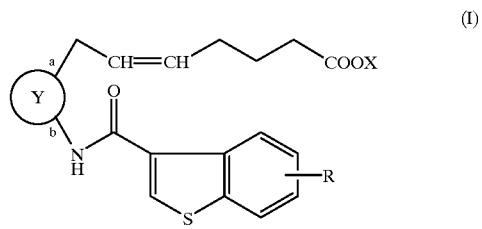

(I)

wherein

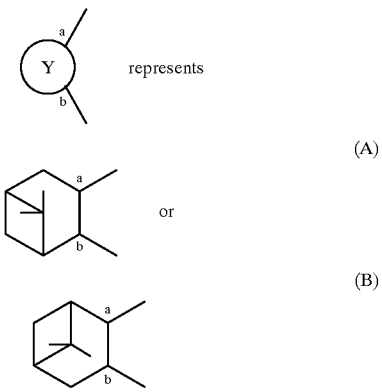

represents

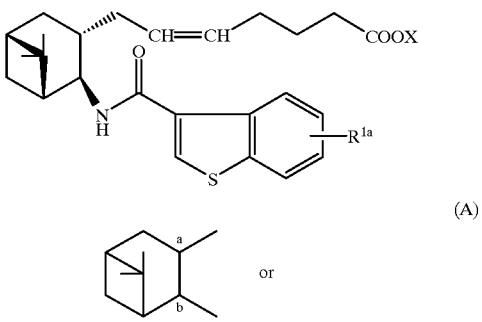

(A)

or

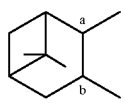
(B)

R represents hydrogen, alkyl, alkoxy, halogen, hydroxy, acyloxy or optionally substituted arylsulfonyloxy, X represents hydrogen or alkyl, and the double bond on the α-chain has E configuration or Z configuration, provided that the compound of the formula:

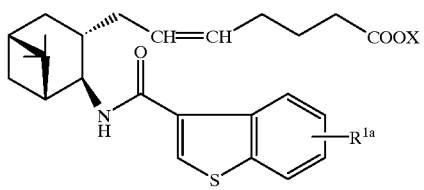

wherein $R^{1a}$ represents hydrogen, alkyl or alkoxy, X is as defined above, and the double bond on the α-chain has E configuration or Z configuration is excluded, a pharmaceutically acceptable salt thereof, or a hydrate thereof.

In the present specification, in the formula (I), the linkage represented by the group:

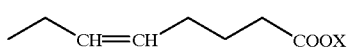

wherein X is as defined above;
is referred to as α-chain, the linkage represented by the group:

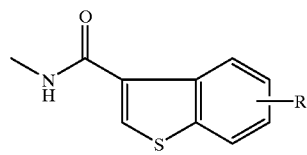

wherein R is as defined above;
is referred to as ω-chain.

The double bond on the α-chain has E configuration or Z configuration.

BEST MODE FOR CARRYING OUT THE INVENTION

Figure 1:
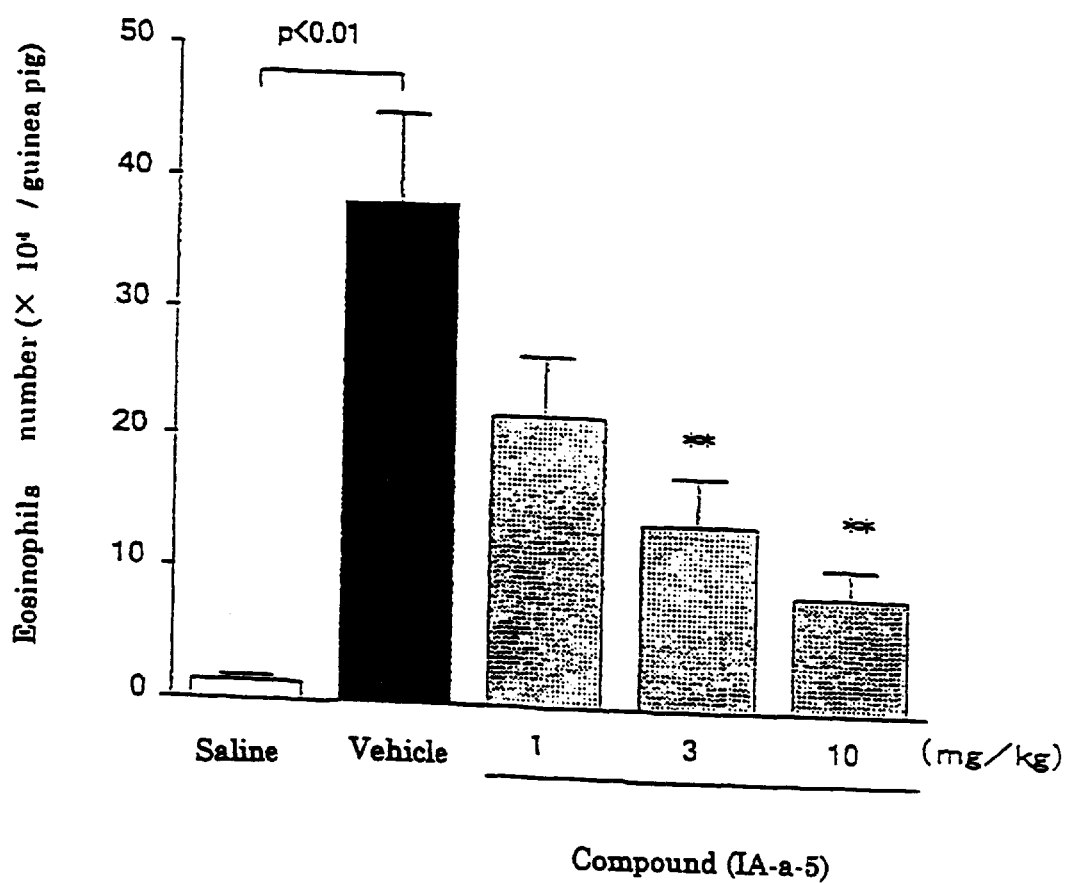
FIG. 1 shows the activity of the compound (IA-a-5) against infiltration of eosinophils in the nasal cavity induced by an antigen. In the figure, the white column indicates a group to which saline was inhaled instead of ovalbumin; the black column indicates a group to which an antigen was inhaled to induce an inflammatory reaction but not administered the compound (IA-a-5); and the gray columns indicate groups to which an antigen was inhaled to induce an inflammatory reaction and administered the compound (IA-a-5). The asterisk ** indicate significantly different from vehicle at p<0.01.

More specifically, the compounds (I) can be exemplified by a compound of the formula (IA):

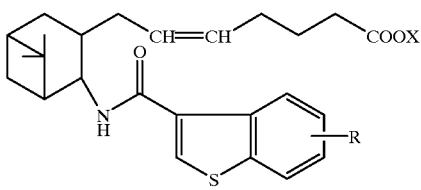
(IA)

wherein R and X are as defined above, and the double bond on the α-chain has E configuration or Z configuration, provided that the compound of the formula:

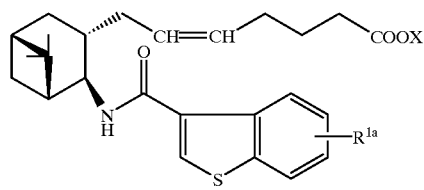

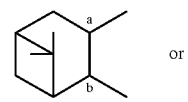
(A)

or

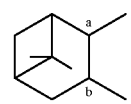
(B)

wherein $R^{1a}$ represents hydrogen, alkyl or alkoxy, X is as defined above, and the double bond on the α-chain has E configuration or Z configuration is excluded, a pharmaceutically acceptable salt thereof, or a hydrate thereof.

Similarly, the compounds (I) can also be exemplified by the compound of the formula (IB):

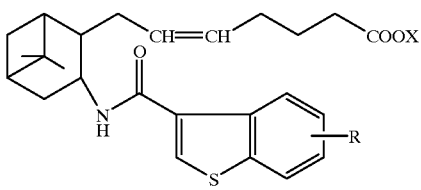
(IB)

wherein R and X are as defined above, and the double bond on the α-chain has E configuration or Z configuration, a pharmaceutically acceptable salt thereof, or a hydrate thereof.

More specifically, the compounds of the formula (IA) can be exemplified by:

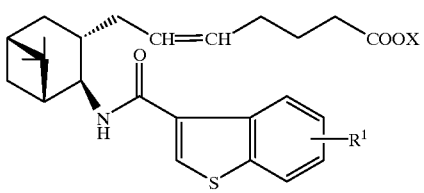
(IA-a)

-continued

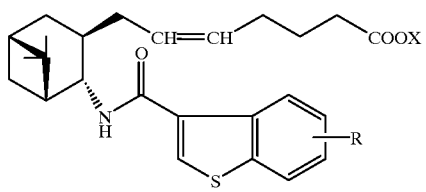
(IA-b)

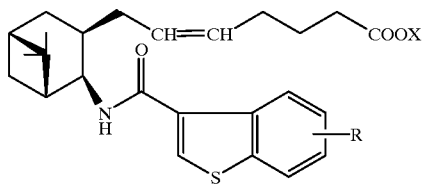
(IA-c)

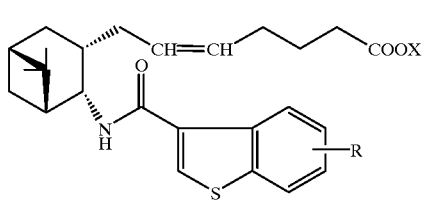
(IA-d)

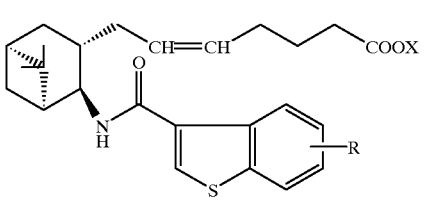
(IA-a')

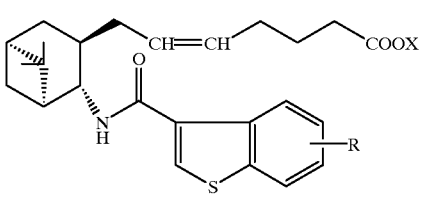
(IA-b')

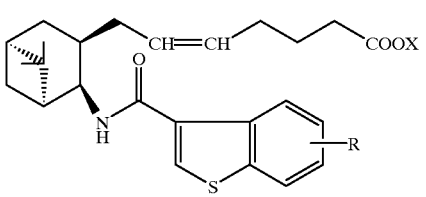
(IA-c')

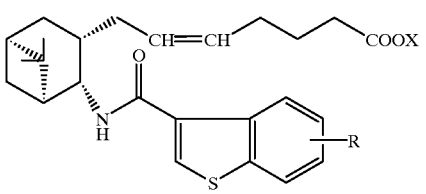
(IA-d')

wherein $R^1$ represents halogen, hydroxy, acyloxy or optionally substituted arylsulfonyloxy, R and X are as defined above, and the double bond on the α-chain has E configuration or Z configuration.

Preferred examples of the compounds include those of the formula (IA-a), (IB-b), (IA-c), (IA-d) and (IA-b').

Particularly, preferred examples of the compounds include those of the formula (IA-a).

Similarly, the compounds of the formula (IB) can be exemplified by:

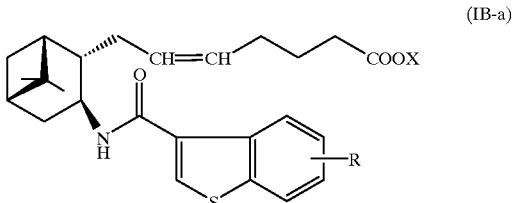
(IB-a)

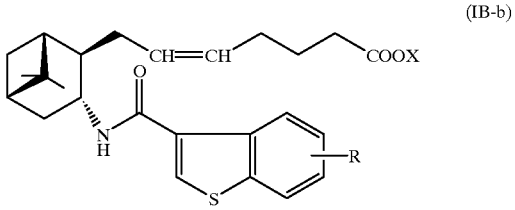
(IB-b)

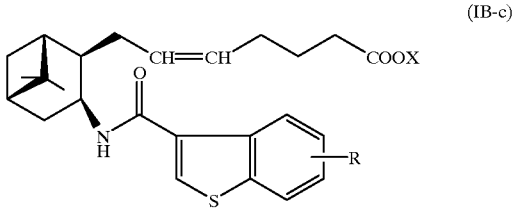
(IB-c)

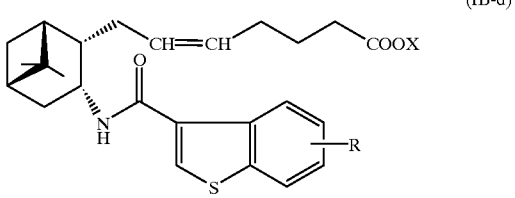
(IB-d)

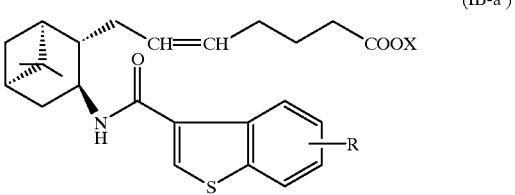
(IB-a')

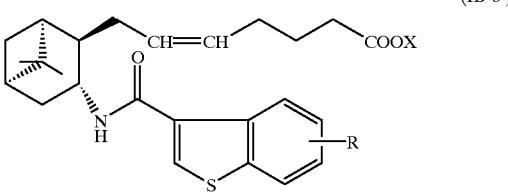
(IB-b')

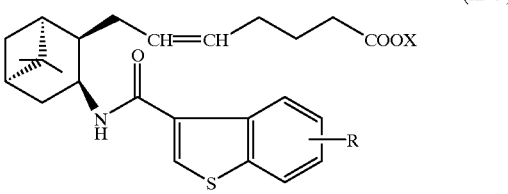
(IB-c')

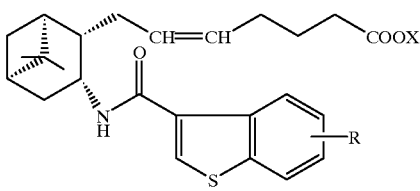

(IB-d')

wherein R and X are as defined above, and the double bond on the α-chain has E configuration or Z configuration.

Preferred examples of the compounds include those of the formula (IB-a') and (IB-b').

Another examples of the compounds include those wherein the double bond on the α-chain has E configuration of the formula (I), (IA), (IB), (IA-a), (IA-b), (IA-c), (IA-d), (IA-b'), (IB-a') and (IB-b').

Similarly, examples of the compounds include those wherein the double bond on the α-chain has Z configuration of the formula (I), (IA), (IB), (IA-a), (IA-b), (IA-c), (IA-d), (IA-b'), (IB-a') and (IB-b').

Similarly, examples of the compounds include those wherein R is bromo, fluoro, hydroxy, acetoxy, or phenylsulfonyl, and X is hydrogen of the formula (I), (IA), (IB), (IA-a), (IA-b), (IA-c), (IA-d), (IA-b'), (IB-a') and (IB-b').

Similarly, examples of the compounds include those wherein R is hydrogen, methyl or methoxy, and X is hydrogen of the formula (I), (IA), (IB), (IA-b), (IA-c), (IA-d), (IA-b'), (IB-a') and (IB-b').

As for examples of the intermediates include compounds of the formula (V):

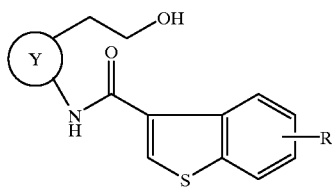

(V)

wherein the Y ring and R are as defined above.

Another examples of the intermediates include compounds of the formula (VI):

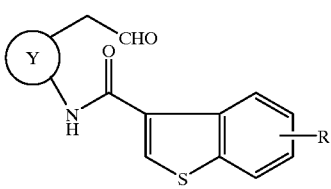

(VI)

wherein the Y ring and R are as defined above.

Another examples of the intermediates include compounds of the formula (IIIa):

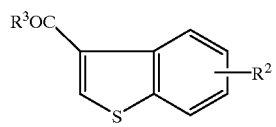

(IIIa)

wherein $R^2$ represents acyloxy or optionally substituted arylsulfonyloxy, and $R^3$ represents hydroxy or halogen.

Preferred examples of the compounds include those of the formula (IIIb):

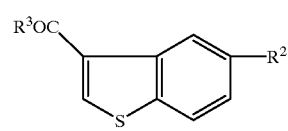

(IIIb)

wherein $R^2$ and $R^3$ are as defined above, or the formula (IIIc):

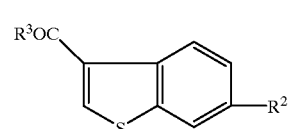

(IIIc)

wherein $R^2$ and $R^3$ are as defined above.

Particularly, preferred examples of the compounds include those wherein $R^3$ is hydroxy, or $R^2$ is phenylsulfonyloxy or acetyloxy of the formula (IIIa), (IIIb) and (IIIc).

Another embodiment of the present invention is a pharmaceutical composition comprising the compound of the formula (I) or a $PGD_2$ antagonist comprising them. Particularly, the compounds of the formula (I) are useful as drugs for treating nasal blockage. $PGD_2$ antagonists in the present invention inhibit infiltration of inflammatory cells. The term "inflammatory cells" means all of lymphocytes, eosionophils, neutrophils, and macrophages, and particularly, eosionophils.

The compounds (I) in the present invention show $PGD_2$-antagonistic activities through the binding to $PGD_2$ receptor, so they are useful as drugs for treating diseases in which mast cell dysfunction due to excessive production of $PGD_2$ is involved. For example, the compounds (I) are useful as drugs for treating diseases, such as systemic mastocytosis and disorder of systemic mast cell activation as well as for tracheal contraction, asthma, allergic rhinitis, allergic conjunctivitis, urticaria, ischemic reperfusion injury, inflammation and atopic dermatitis. Moreover, the compounds (I) of the present invention possess an activity inhibiting infiltration of inflammatory cells. The compounds (I) are especially useful as drugs for treating nasal blockage.

The terms used throughout the present specification are as defined below.

The term "halogen" means fluoro, chloro, bromo and iodo.

The term "acyl" in the "acyloxy" means $C_1$–$C_9$ acyl derived from aliphatic carboxylic acid, for example, formyl, acetyl, propionyl, butyryl, valeryl, and the like. The term "acyloxy" means acyloxy derived from the above-mentioned acyl, for example, acetoxy, propionyloxy, butyryloxy, valeryloxy, and the like.

The term "aryl" means $C_6$–$C_{14}$ monocyclic or condensed ring, for example, phenyl, naphthyl (e.g., 1-naphthyl, 2-naphtyl), anthryl (e.g., 1-anthryl, 2-anthryl, 9-anthryl), and the like. The substituents on the aryl include alkyl, alkoxy, halogen, hydroxy, and the like.

The term "alkyl" means $C_1-C_6$ straight or branched chain alkyl, for example, methyl, ethyl, n-propyl, i-propyl, n-butyl, i-butyl, s-butyl, t-butyl, n-pentyl, i-pentyl, neopentyl, t-pentyl, hexyl, and the like.

The term "alkoxy" means $C_1-C_6$ alkoxy, for examples, methoxy, ethoxy, n-propoxy, i-propoxy, n-butoxy, and the like.

Examples of salts of the compounds (I) include those formed with an alkali metal (e.g., lithium, sodium or potassium), an alkali earth metal (e.g., calcium), an organic base (e.g., tromethamine, trimethylamine, triethylamine, 2-aminobutane, t-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine or pyridine), an amino acid (e.g., lysine, or arginine), and the like.

Examples of hydrates of the compounds represented by the formula (I) may be coordinated with the compound (I) at the optional proportion.

The compounds represented by the formula (I) represent the optional steric configuration, the double bone on the α-chain has E configuration or Z configuration, the bond binding to the bicyclic ring represents R configuration or S configuration, and include the all isomers (diastereomers, epimers, enantiomers, and the like), racemates and mixtures thereof.

General processes for the preparation of the compounds in the present invention can be illustrated as follows. In the case of the compounds having substituents which interfere the reaction, such substituents may preliminarily be protected with protecting groups, and they may be removed in the suitable step.

PROCESS 1

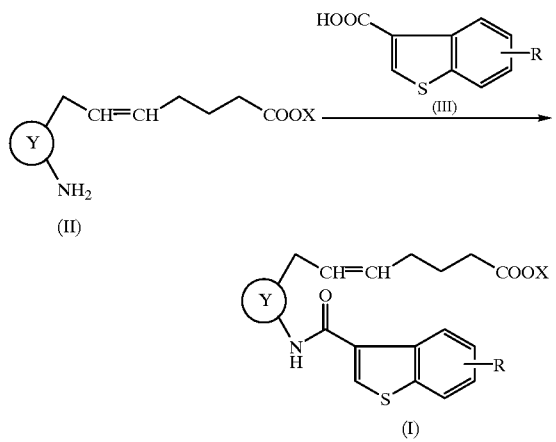

wherein the Y ring, X and R are as defined above, and the double bond on the α-chain has E configuration or Z configuration.

The compounds of the formula (I) as shown in the above process 1 can be prepared by reacting a carboxylic acid of the formula (III) or their reactive derivatives with an amino compounds of the formula (II).

In this process, the starting compounds (II) wherein

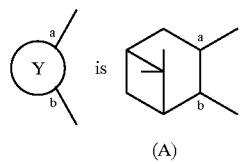

(A)

are described in the Japanese Patent Publication (Kokoku) No. 23170/1994. The compounds (II) wherein

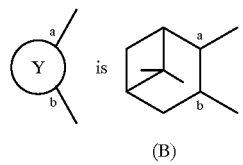

(B)

are described in the Japanese Patent Publication (Kokai) Nos. 49/1986 and 180862/1990.

The carboxylic acid of the formula (III) includes 4-bromobenzo[b]thiophene-3-carboxylic acid, 5-bromobenzo[b]thiophene-3-carboxylic acid, 6-bromobenzo[b]thiophene-3-carboxylic acid, 7-bromobenzo[b]thiophene-3-carboxylic acid, 5-fluorobenzo[b]thiophene-3-carboxylic acid, 6-fluorobenzo[b]thiophene-3-carboxylic acid, 4-hydroxybenzo[b]thiophene-3-carboxylic acid, 5-hydroxybenzo[b]thiophene-3-carboxylic acid, 6-hydroxybenzo[b]thiophene-3-carboxylic acid, 7-hydroxybenzo[b]thiophene-3-carboxylic acid, 5-acetoxybenzo[b]thiophene-3-carboxylic acid, benzo[b]thiophene-3-carboxylic acid, and 5-benzosulfonyloxybenzo[b]thiophene-3-carboxylic acid, 5-methylbenzo[b]thiophene-3-carboxylic acid, 6-methylbenzo[b]thiophene-3-carboxylic acid, 5-methoxybenzo[b]thiophene-3-carboxylic acid, 6-methoxybenzo[b]thiophene-3-carboxylic acid. These carboxylic acids may have the substituents as defined above.

These carboxylic acids can be prepared in accordance with methods as described in Nippon Kagaku Zasshi Vo.l 88, No. 7, 758–763 (1967), Nippon Kagaku Zasshi Vol. 86, No. 10, 1067–1072 (1965), J. Chem. Soc (c) 1899–1905 (1967), J. Heterocycle. Chem. Vol. 10 679–681 (1973), J. Heterocyclic Chem. Vol 19 1131–1136 (1982) and J. Med. Chem. Vol. 29 1637–1643 (1986).

The reactive derivative of carboxylic acid of the formula (III) means the corresponding acid halide (e.g., chloride, bromide, iodide), acid anhydride (e.g., mixed acid anhydride with formic acid or acetic acid), active ester (e.g., succinimide ester), and the like, and can generally be defined as acylating agents used for the acylation of amino group. For example, when an acid halide is employed, the compound (III) is reacted with a thionyl halide (e.g., thionyl chloride), phosphorous halide (e.g., phosphorous trichloride, phosphorous pentachloride), oxalyl halide (e.g., oxalyl chloride), and the like, in accordance with known methods as described in the literatures (e.g., Shin-Jikken-Kagaku-Koza Vol. 14, 1787 (1978); Synthesis 852–854 (1986); Shin-Jikken-Kagaku-Koza Vol. 22, 115 (1992)).

The reaction can be conducted under a condition generally used for the acylation of amino group. For example, in the case of condensation with the acid halide, the reaction is carried out in a solvent such as an ether solvent (e.g., diethyl ether, tetrahydrofuran, dioxane), benzene solvent (e.g., benzene, toluene, xylene), halogenated solvent (e.g., dichloromethane, dichloroethane, chloroform) as well as ethyl acetate, dimethylformamide, dimethyl sulfoxide, acetonitrile, and those aqueous solvents, or the like, if necessary, in the presence of a base (e.g., organic base such as triethylamine, pyridine, N,N-dimethylaminopyridine, N-methylmorpholine; inorganic base such as sodium hydroxide, potassium hydroxide, potassium carbonate, or the like) under cooling at room temperature or under heating, preferably at a temperature ranging from −20° C. to ice-cooling temperature, or from room temperature to a refluxing temperature of the reaction system, for a period of several min to several hr, preferably for 0.5 hr to 24 hr, particularly, for 1 hr to 12 hr. In the case of using the carboxylic acid in a free form without converting into the reactive derivatives, the reaction is conducted in the presence of a condensing agent (e.g., dicyclohexylcarbodiimide (DCC), 1-ethyl-3-(3-methylaminopropyl)carbodiimide, N,N'-carbonyldiimidazole) usually used in the condensation reaction.

The compound (I) of the present invention can be also prepared in accordance with a method as follows.

PROCESS 2

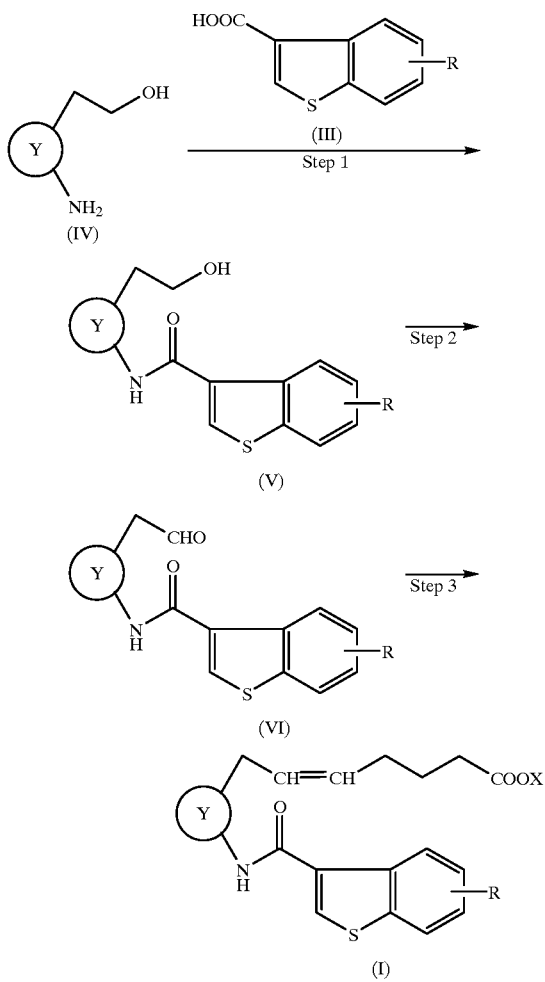

wherein the Y ring, R and X are as defined above, and the double bond on the α-chain has E configuration or Z configuration.

(Step 1)

In this step, a compound of the formula (V) can be prepared by reacting an amino compound of the formula (IV) with the carboxylic acid of the formula (III) or its reactive derivative, this step can be prepared in accordance with the same process as process 1. Some of the amino compound of the formula (IV) is described that the process is disclosed in Chem. Pharm. Bull. Vol. 37, No. 6, 1524–1533 (1989).

(Step 2)

In this step, the compound of the formula (V) is oxidized into the aldehyde compound of the formula (VI). This step may be carried out with chromated oxidizing agents such as Jones' reagent, Collins' reagent, pyridinium chlorochromate, pyridinium dichromate in a solvent such as chlorinated hydrocarbon (e.g., chloroform, dichloromethane), ether (e.g., ethyl ether, tetrahydrofuran), or acetone, benzene, and the like under cooling or at room temperature for several hours. This step may be also carried out with oxidizing agents in the combination of appropriate activator agents (e.g., trifluoroacetic anhydride, oxalyl chloride), and dimethyl sulfoxide, if necessary, in the presence of base (e.g., organic base such as triethylamine, diethylamine).

(Step 3)

In this step, the α-chain of the aldehyde compound of the formula (VI) is conducted into the compound of the formula (I). In this step, the compound of the formula (I) can be prepared by reacting the aldehyde compound of the formula (VI) with an ylide compound corresponding to the rest part of the α-chain in accordance with conditions of the Wittig reaction. Further, the ylide compound corresponding to the rest part of the α-chain can be synthesized by reacting triphenylphosphine with a corresponding halogenated alkanoic acid or ester derivative thereof in the presence of a base according to a known method.

In the reaction of the other reactive derivatives or free acid with the amine (II) or (IV), according to the property of each reactive derivatives or free acid, in accordance with a known method, the reaction conditions are determined. The reaction product can be purified in accordance with a conventional purification, such as the extraction with a solvent, chromatography, recrystallization, and the like.

The objective compound (I) in the present invention can be converted into a corresponding ester derivative, if desired. For example, the ester can be prepared by esterification the carboxylic acid in accordance with a known method. If desired, E isomer, Z isomer or the mixtures can be produced depending on the reaction conditions.

When using a compound (I) of the present invention in treatment, it can be formulated into ordinary formulations for oral and parenteral administration. A pharmaceutical composition containing a compound (I) of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulation, carriers, excipients, solvents, and bases known to one ordinary skilled in the art may be used. In case of tablets, they are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated approximately. In the case of liquid formulations such as syrups, solutions, or suspensions, they may contain suspending agents (e.g., methyl cellulose), emulsifiers (e.g., lecithin), preservatives and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension. Especially, in the case of nasal drug for treating nasal blockage, it can be used as a solution or suspension prepared by a conventional formulating method, or as a powder formulated using a powdering agent (e.g., hydroxypropyl cellulose, carbopole), which are administered into the nasal cavity. Alternatively, it can be used as an aerosol after filling into a special container together with a solvent of low boiling point.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between about 0.01–100 mg, preferably about 0.01–10 mg, more preferably about 0.01–1 mg, per kg body weight. In the case of parenteral administration, the daily dosage can generally be between about 0.001–100 mg, preferably about 0.001–1 mg, more preferably about 0.001–0.1 mg, per kg body weight. The daily dosage can be administered in 1–4 divisions.

The following Examples are provided to further illustrate the present invention and are not to be construed as limiting the scope.

The abbreviation used throughout the examples in the present invention are shown as follows.

| Me | methyl |
| Ac | acetyl |
| Ph | phenyl |

REFERENCE 1

Preparation of 5-Benzenesulfonyloxybenzo[b]thiophene-3-carbonyl chloride (3)

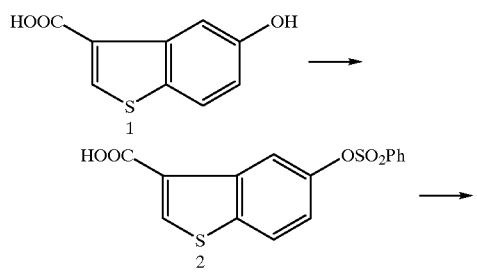

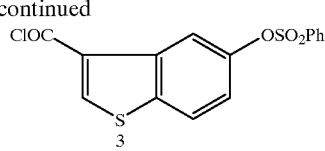

To a solution of 8.63 g (44.4 mol) of 5-hydroxybenzo[b]thiophene-3-carboxylic acid (1) (J. Chem. Soc (C), 1899–1905 (1967), M.Martin-Smith et al.) in 160 ml of 80% aqueous tetrahydrofuran and 44 ml of 1N sodium hydroxide was added 87 ml of 0.56N sodium hydroxide and 6.2 ml (48.4 mmol) of benzenesulfonylchloride simultaneously with keeping at pH 11–12 with stirring under ice-cooling. After the reaction completion, the mixture was diluted with water, alkalized and washed with toluene. The aqueous layer was weakly acidified with conc. hydrochloric acid under stirring. The precipitated crystals were filtered, washed with water, and dried to give 14.33 g of 5-benzenesulfonyloxybenzo[b]thiophene-3-carboxylic acid (2).

mp 202–203° C. NMR δ (CDCl$_3$), 300 MHz 7.16 (1H, dd, J=2.7 and 9.0 Hz), 7.55–7.61 (2H, m), 7.73 (1H, m) 7.81 (1H, d, J=9.0 Hz), 7.90–7.94 (2H, m), 8.16 (1H, d, J=2.7 Hz), 8.60 (1H, s). IR (Nujol): 3102, 2925, 2854, 2744, 2640, 2577, 1672, 1599, 1558, 1500, 1460, 1451 cm$^{-1}$ Elemental analysis (for $C_{15}H_{10}O_5S_2$) Calcd. (%): C, 53.88; H, 3.01; S, 19.18 Found (%): C, 53.83; H, 3.03; S, 19.04

A mixture of 5.582 g (16.7 mmol) of the above obtained 5-benzenesulfonyloxybenzo[b]thiophene-3-carboxylic acid (2), a drop of dimethylformamide, 3.57 ml (50 mmol) of thionyl chloride and 22 ml of toluene was refluxed for 1.5 hours, and then concentrated under reduced pressure to give 5.89 g of the objective compound (3).

REFERENCE 2

Preparation of 5-Acetoxybenzo[b]thiophene-3-carbonyl chloride (5)

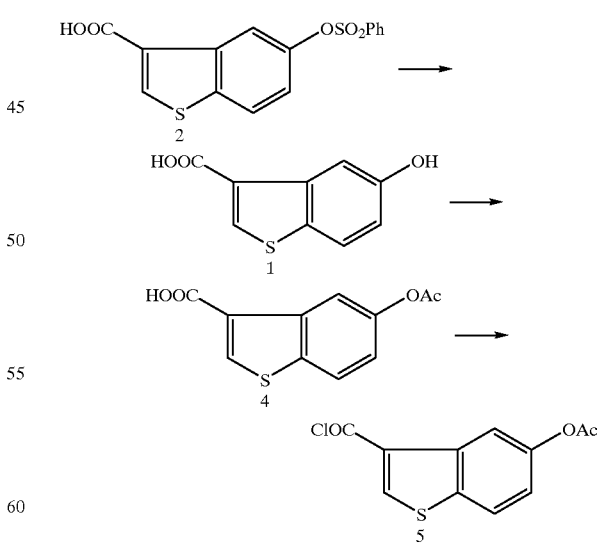

A solution of 100 mg (0.3 mmol) of the above obtained 5-benzenesulfonyloxybenzo[b]thiophene-3-carboxylic acid (2) in 1.2 ml of 1N sodium hydroxide was allowed to stand for 8 hours at 40° C. Hydrochloric acid (1N, 1.2 ml) was added thereto, and the precipitated crystals were filtered, washed with water, and dried to give 58 mg of 5-hydroxybenzo[b]thiophene-3-carboxylic acid (1). Yield 96.6% mp 262–263° C.

A solution of 1,140 mg of the above obtained 5-hydroxybenzo[b]thiophene-3-carboxylic acid (1) in 2 ml of acetic anhydride and 4 ml of pyridine was allowed to stand for 3 hours. After addition of water, the mixture was stirred for 1.5 hours under ice-cooling, and the precipitated crystals were filtered, washed with water, and dried to give 1,349 mg of 5-acetoxybenzo[b]thiophene-3-carboxylic acid (4). Yield 97.3%. mp 239–240° C.

A mixture of 1,349 mg of the above obtained 5-acetoxybenzo[b]thiophene-3-carboxylic acid (4), a drop of dimethylformamide, 1.22 ml of (17.13 mmol) of thionyl chloride and 25 ml of toluene was refluxed for 1.5 hours, and then concentrated under reduced pressure to give 1,454 mg of the objective compound (5).

REFERENCE 3

Preparation of (1R, 2S, 3S, 5S)-2-(2-Amino-6,6-dimethylbicyclo[3.1.1]hept-3-yl)ethanol (IVA-b-1) and (1R, 2R, 3S, 5S)-2-(2-Amino-6,6-dimethylbicyclo[3.1.1]hept-3-yl)ethanol (IVA-c-1)

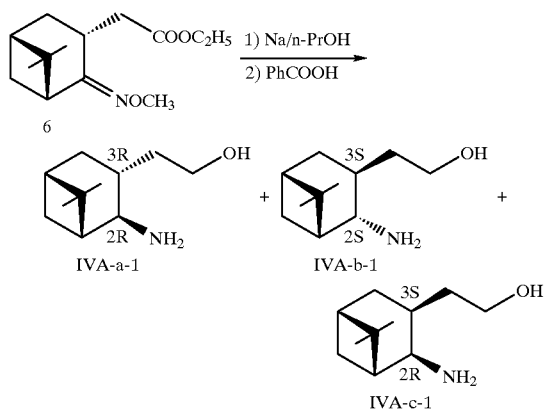

the compound (6) (Chem. Pharm. Bull. Vol.37, No.6 1524–1533 (1989)) was reduced with sodium according to the method described in the above literature, and the compound (IVA-a-1) was removed by filtration as the benzoic acid salt. The mother liquor (79 g) was suspended in 150 ml of ethyl acetate, added 260 ml of 1N-hydrochloric acid, and stirred. The aqueous layer separated from the two layers was basified with 65 ml of 4N-sodium hydroxide, and extracted with ethyl acetate. The organic layer was washed with water, and dried over anhydrous magnesium sulfate and concentrated under reduced pressure. The obtained oily residue (6.7 g of 30 g) was dissolved in 40 ml of 90% methanol, absorbed by 500 ml of an ion-exchange resin, Amberlite CG-50 ($NH_4^+$) type I, and eluted with 2.2 L of water and 1N-2.2 L of aqueous ammonia by a gradient method. One fraction: 300 ml. Each fraction was checked by thin-layer chromatography (the developing solvent; chloroform; methanol: conc. aqueous ammonia=90:10:1). The fractions 3–8 were collected, and concentrated under reduced pressure. The residue was crystallized from hexane; recrystallization afforded 538 mg of needles.

mp 117–118° C. NMR δ (CDCl$_3$), 300 MHz 1.01 and 1.21 (each 3H, each s), 1.34 (1H, d, J=9.9 Hz), 1.52–1.66 (2H, m), 1.90–2.07 (4H, m), 218 (1H, m), 2.48 (1H, m), 3.12 (3H, bs), 3.49 (1H, dd, J=3.9 and 9.6 Hz), 3.61 (1H, dt, J=2.4 and 10.5 Hz), 3.84 (1H, ddd, J=3.3, 4.8 and 10.5 Hz). IR (Nujol): 3391, 3293, 3108, 2989, 2923, 2869, 2784, 2722, 2521, 1601, 1489, 1466 cm$^{-1}$ [α]$_D^{23}$-2.5° (c=1.02, CH$_3$OH) Elemental analysis for (C$_{11}$H$_{21}$NO) Calcd.: (%): C, 72.08; H, 11.55; N, 7.64 Found: (%): C, 72.04; H, 11.48; N, 7.58

By means of X-ray crystal analysis, the structural formula was identified as that of (1R, 2R, 3S, 5S)-2-(2-amino-6,6-dimethylbicyclo[3.1.1]hept-3-yl)ethanol (IVA-c-1). The mother liquor (2.9 g) after the recrystallization from hexane was dissolved in 15 ml of ethyl acetate, to which was added a solution of 30 ml of ethyl acetate containing 1.93 g of benzoic acid. The precipitated crystals were filtered to give 2.93 g of the benzoic acid salt of the compound (IVA-a-1).

mp 182–183° C.

The fractions 10–17 were collected and concentrated under reduced pressure. To a solution of 2.66 g of the residue in 15 ml of ethyl acetate was added 11 ml of ethyl acetate containing 1.77 g of benzoic acid. The precipitated crystals were filtered to give 4.08 g of needles.

mp 160–161° C. NMR δ (CDCl$_3$), 300 MHz 0.61 and 1.06 (each 3H, each s), 1.36 (1H, m), 1.53–1.65 (2H, m), 1.75–1.88 (2H, m), 1.95–2.04 (4H, m), 3.18 (1H, d, J=6.3 Hz), 3.58 (1H, dt, J=3.0 and 10.8 Hz), 3.81 (1H, m), 5.65 (4H, bs), 7.33–7.42 (3H, m), 7.98–8.01 (2H, m). IR (Nujol): 3320, 2922, 2854, 2140, 1628, 1589, 1739, 1459, 1389 cm$^{-1}$ [α]$_D^{23}$-31.8° (c=1.01, CH$_3$OH) Elemental analysis (for C$_{18}$H$_{27}$NO$_3$) Calcd.: (%): C, 70.79; H, 8.91; N, 4.59 Found: (%): C, 70.63; H, 8.86; N, 4.58

By means of X-ray crystal analysis, the structural formula was identified as that of (1R, 2S, 3S, 5S)-2-(2-amino-6,6-dimethylbicyclo[3.1.1]hept-3-yl)ethanol (IVA-b-1).

EXAMPLE 1

Preparation of Sodium (5Z)-7-{(1R,2R,3S,5S)-2-(5-hydroxybenzo[b]thiophen-3-yl-carbonylamino)-6,6-dimethylbicyclo[3.1.1]hept-3-yl}-5-heptenoate (IA-a-6)

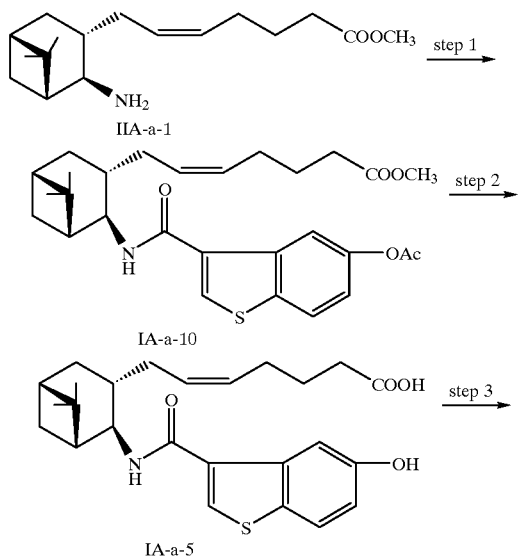

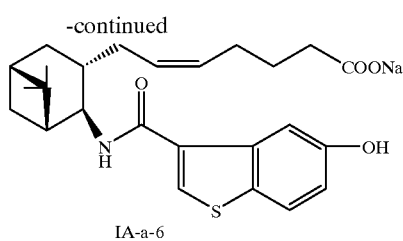

IA-a-6

(Step 1)

to a solution of 1,450 mg (5.2 mmol) of a compound (IIA-a-1) (Japanese Patent Publication (Kokoku) No. 23170/1994) in 25 ml of tetrahydrofuran were added 2.6 ml (18.7 mmol) of triethylamine and 1,454 mg (1.1 mmol) of 5-acetoxybenzo[b]thiophene-3-carbonyl chloride (5) obtained by the reference 2. After stirring for 1.5 hours, the mixture was diluted with water, and extracted with toluene. The organic layer was washed with dilute hydrochloric acid and water, dried over anhydrous magnesium sulfate, and concentrated under reduced pressure. The residue was chromatographed on silica gel (toluene:ethyl acetate=9:1) to give 2,481 mg of the compound (IA-a-10). Yield 96.1%. $[\alpha]D^{23}=+48.0°$ (c=1.01%, $CH_3OH$) Elementary Analysis (for $C_{28}H_{35}NO_5S.0.1H_2O$) Calcd. (%): C, 67.34; H, 7.10; N, 2.80; S, 6.42 Found (%): C, 67.23; H, 7.12; N, 2.86; S, 6.59

(Step 2)

To a solution of 2,357 mg (4.73 mmol) of the above obtained compound (IA-a-10) in 25 ml of methanol was added 4.1 ml (16.4 mmol) of 4N-sodium hydroxide. After stirring for 6 hours, the mixture was neutralized with 17 ml of 1N-hydrochloric acid, diluted with water, and extracted with ethyl acetate. The organic layer was washed with water, dried over magnesium sulfate and concentrated under reduced pressure. The residue as recrystallized from ethyl acetate/n-hexane to give 1,859 mg of the compound (IA-a-5) as prisms. Yield 86.5%.

mp 142–143° C. $[\alpha]D^{23}=+47.6°$ (c=1.01%, $CH_3OH$) Elementary Analysis (for $C_{25}H_{31}NO_4S$) Calcd. (%): C, 68.00; H, 7.08; N, 3.17; S, 7.26 Found (%): C, 67.93; H, 7.08; N, 3.19; S, 7.24

(Step 3)

To a solution of 203 mg (0.46 mmol) of the above obtained compound (IA-a-5) in 3 ml of methanol was added 0.42 ml (0.42 mmol) of 1N-sodium hydroxide, and the mixture was concentrated under reduced pressure. The residue was dissolved in a small quantity of ethyl acetate, and diluted with n-hexane. The insoluble material was dissolved in methanol, and concentrated under reduced pressure to give 210 mg of the objective compound (IA-a-6). Yield 98.5%. $[\alpha]D^{25}=+38.9°$ (c=1.00%, $CH_3OH$) Elementary Analysis (for $C_{25}H_{30}NO_4SNa.0.5H_2O$) Calcd. (%): C, 63.54; H, 6.61; N, 2.96; S, 6.78; N a, 4.86 Found (%): C, 63.40; H, 6.69; N, 3.13; S, 6.73; Na, 4.68

EXAMPLE 2

Preparation of (5Z)-7-[(1R,2S,3R,5S)-2-(5-hydroxybenzo[b]thiophen-3-yl-carbonylamino)-6,6-dimethyl-bicyclo[3.1.1]hept-3-yl]-5-heptenoic acid (IA-b-1)

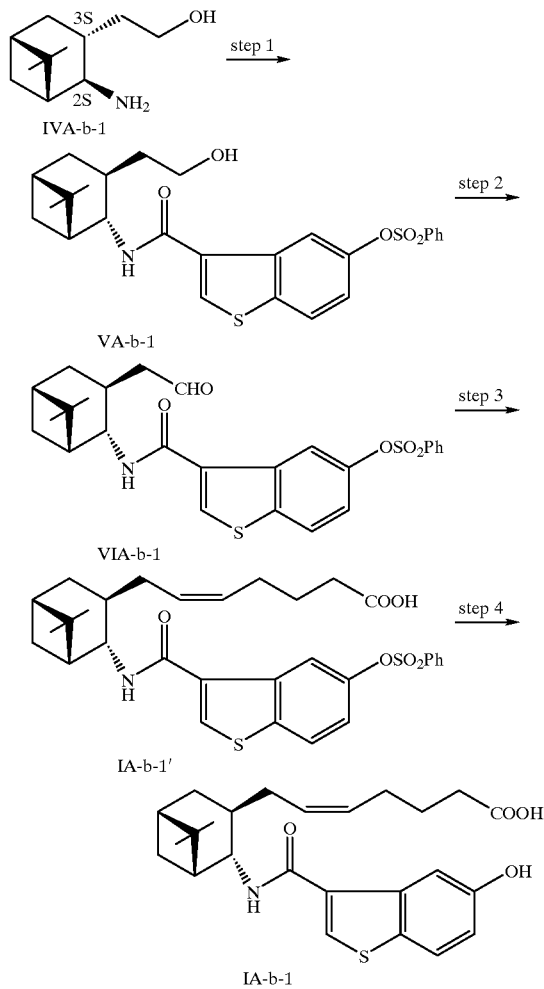

(Step 1)

To a suspension of 916 mg (3 mmol) of (1R,2S,3S,5S)-2-(2-amino-6,6-dimethylbicyclo[3.1.1]hept-3-yl)ethanol benzoic acid salt in 3 of water was added 3.1 ml of 1N hydrochloric acid. The precipitated benzoic acid was extracted with ethyl acetate. The aqueous layer was adjusted at pH 10.5 with 700 mg of anhydrous sodium carbonate, to which was dropwise added a solution of 1.06 g (3 mmol) of 5-benzenesulfonyloxybenzo[b]thiophene-3-carbonyl chloride (3) in 6 ml of tetrahydrofuran. After 1.5 hours, the mixture was diluted with water and extracted with toluene. The organic layer was washed with water, dried over anhydrous magnesium sulfate, and concentrated under reduced pressure. The thus-obtained residue (1.5 g) was chromatographed on silica gel (hexane: ethyl acetate=1.1) to give 1.497 g of the compound (VA-b-1). Yield 99.8%. $[\alpha]D^{\cong}-31.1°$ (c=1.00, $CH_3OH$) Elemental analysis (for $C_{26}H_{29}NO_5S_2.0.2H_2O$) Calcd. (%): C, 62.05; H, 5.89; N, 2.78; S, 12.74 Found (%): C, 62.03; H, 5.93; N, 2.79; S, 12.72

(Step 2)

A solution of 0.61 ml (8.6 mmol) of dimethylsulfoxide in 9.7 ml of 1,2-dimethoxyethane was cooled at −60° C., to which was dropwise added 0.37 ml (4.3 mmol) of oxalyl chloride. After 15 minutes, a solution of 1.427 g (2.9 mmol) of the above obtained compound (VA-b-1) in 11 ml of 1,2-dimethoxyethane was added thereto. After stirring for 30 minutes, 1.2 m of triethylamine was added, and the mixture was stirred for 30 minutes, and warmed up gradually to room temperature. The mixture was diluted with water and extracted with toluene. The organic layer was washed with water, dried over anhydrous magnesium sulfate, and concentrated under reduced pressure. The thus-obtained residue was chromatographed on silica gel (hexane: ethyl acetate= 6:4) to give 1.338 g of the compound (VIA-b-1). Yield 94.1%. $[\alpha]D^{24}$-29.1° (c=1.01, $CH_3OH$) Elemental analysis (for $C_{26}H_{27}NO_5S_2 \cdot 0.4H_2O$) Calcd. (%): C, 61.85; H, 5.55; N, 2.77; S, 12.70 Found (%): C, 61.92; H, 5.60; N, 2.79; S, 12.88

(Step 3)

A suspension of 1.72 g (3.9 mmol) of 4-carboxybutyltriphenylphosphonium bromide and 1.016 g (9 mmol) of potassium t-butoxide in 9 ml of tetrahydrofuran was stirred for 1 hour under ice-cooling. To the mixture was added a solution of 1.288 g (2.6 mmol) of the above obtained compound (VIA-b-1) in 4 ml of tetrahydrofuran over 6 minutes, and the mixture was stirred at the same temperature for 2 hours. The mixture was diluted with 15 ml of water, acidified to pH 10.5 with 1N hydrochloric acid, and washed with 15 ml of toluene twice. The aqueous layer was acidified with 1N hydrochloric acid at pH 8.0, added 1.15 g (10.4 mmol) of anhydrous calcium chloride, and extracted with 15 ml of ethyl acetate twice. The organic layer was diluted with 16 ml of water, acidified with 1N hydrochloric acid at pH 2–3, and extracted with ethyl acetate. The organic layer was washed with water, dried over anhydrous magnesium sulfate, and concentrated under reduced pressure to give 1.44 g of the compound (IA-b-1'). Yield 95.5%.

The compound was used for the next step without further purification.

(Step 4)

To a solution of 1.44 g (2.6 mmol) of the above obtained compound (IA-b-1') in 2.8 ml of dimethylsulfoxide was added 3.9 ml of 4N sodium hydroxide, and the mixture was stirred at 55° C. for 3 hours. The mixture was diluted with water washed with 15 of toluene twice. The aqueous layer was acidified with 1 N hydrochloric acid, and extracted with ethyl acetate. The organic layer was washed with water, dried over anhydrous magnesium sulfate, and concentrated under reduced pressure to give 1.097 g of the compound (IA-b-1). Yield 95.9%.

$[\alpha]D^{25}$–43.0° (c=1.01, $CH_3OH$)

Elemental analysis (for $CH_{25}H_{31}NO_4S \cdot 0.2H_2O$)

Calcd. (%): C,67.45; H,7.11; N,3.15; S, 7.20

Found (%): C,67.51; H,7.15; N,3.38; S, 6.96

EXAMPLE 3

Preparation of (5E)-7-[(1R,2R,3S,5S)-2-(5-hydroxybenzo[b]thiophen-3-yl-carbonylamino-6,6-dimethylbicyclo[3.1.1]hept-3-yl]-5-heptenoic acid (IA-a-17)

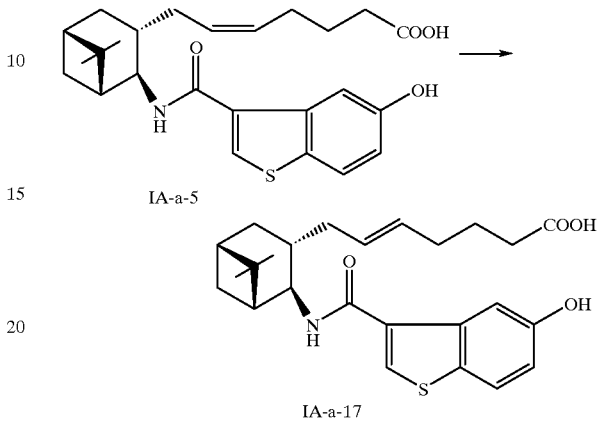

A solution of 11.04 g (25 mmol) of (5Z)-7-[1R,2R,3S, 5S)-2-(5-hydroxybenzo[b]thiophen-3-yl-carbonylamino)-6, 6-dimethyl-bicyclo[3.1.3]hept-3-yl]-5-heptenoic acid (IA-a-5), 4.32 g (18.8 mmol) of 1-methyltetrazol-5-yl disulfide (J. Org. Chem., 50, 2794–2796 (1985), M. Narisada, Y. Terui, M. Yamakawa, F. Watanebe, M. Ohtani, and H. Miyazaki et al.) and 2.84 g (17.3 mmol) of 2,2'-azobisisobutyronitrile in 1.1 L of benzene was refluxed with stirring for 8 hours. The mixture was extracted with 400 ml of 0.4 N sodium hydroxide twice. The aqueous layer was acidified with hydrochloric acid, and the precipitate was collected by filtration. The precipitate (11.08 g) was chromatographed on silica gel (chloroform: methanol=10.0) to give 6.93 g of the compound. The obtained compound was dissolved in 69 ml of dimethoxyethane, to which was added 2.15 g to 4-methoxybenzylamine, and successively diluted with 120 ml of ether under ice-cooling. The precipitate was filtered to give 7.45 of the crystalline product, which was recrystallized from isopropyl alcohol/ethyl acetate/ether (=2/10/5) for purification.

mp 108–111° C.

$[\alpha]D^{23}$+18.9° (c=1.00, $CH_3OH$)

The purity of the isomer of the 4-methoxybenzyamine salt was analyzed by HPLC. Result: (E-isomer):(Z-isomer)= 98.4:1.6.

[HPLC condition] Column: YMG-pac AM-303-10 (10 $\mu$m.120 A.ODS) (4.6 mm Φ X250 mm); flow rate:1 ml/min; detection:UV 254 nm, mobile phase: acetic acid/water/ acetonitrile=0.1/52/48; retention time: (E-isomer) 21 minutes, (Z-isomer) 23 minutes.

The purified 4-methoxybenzylamine salt (1.6 g) was suspended in 25 ml of water, acidified with 25 ml of 1 N-hydrochloric acid and extracted with ethyl acetate. The organic layer was washed with water, dried over anhydrous magnesium sulfate, and concentrated under reduced pressure to give 1.21 g of the compound (IA-a-17).

$[\alpha]D^{24}$+14.4° (c=1.01, $CH_3OH$)

Elemental analysis (for $C_{25}H_{31}NO_4S \cdot 0.1\ H_2O$)

Calcd. (%):C,67.72;H,7.09; N, 3.16;S,7.23

Found (%):C,67;H,7.26; N, 3.35;S,7.39

Compounds and physical constants obtained in the same manner as the above Examples are shown in the following table 11–table 14.
TABLE 1
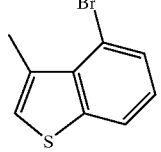
| Compd. No. | X | Z |
|---|---|---|
| IA-a-1 | H | 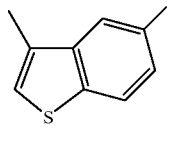 |
| IA-a-2 | H | 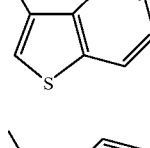 |
| IA-a-3 | H | 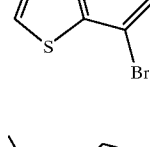 |
| IA-a-4 | H | 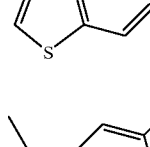 |
| IA-a-5 | H | 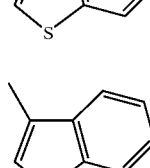 |
| IA-a-6 | Na | 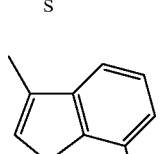 |
| IA-a-7 | H |  |
| IA-a-8 | H | 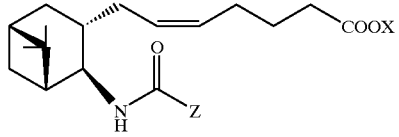 |
TABLE 1-continued
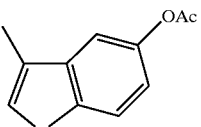
| Compd. No. | X | Z |
|---|---|---|
| IA-a-9 | H | 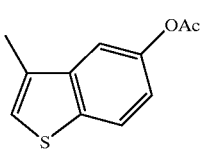 |
| IA-a-10 | CH$_3$ | 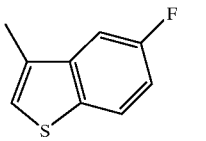 |
| IA-a-11 | H | 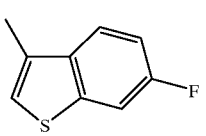 |
| IA-a-12 | H | 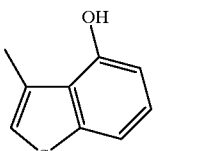 |
| IA-a-13 | H | 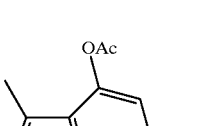 |
| IA-a-14 | H | 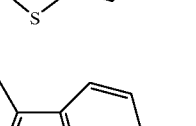 |
| IA-a-15 | H | 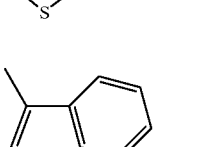 |
| IA-a-16 | H | |

TABLE 2
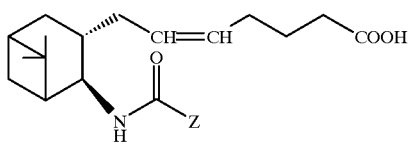
| Compd. No. | |
|---|---|
| IA-a-17 | 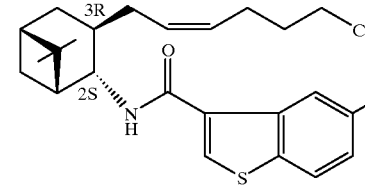 |
| IA-c-1 | 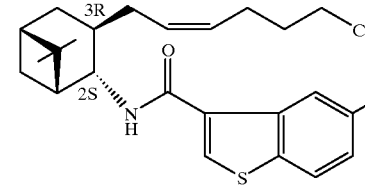 |
| IA-c-2 | 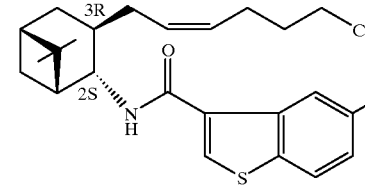 |
| IA-c-3 | 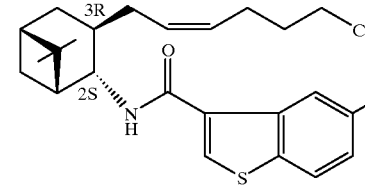 |
| IA-c-4 | 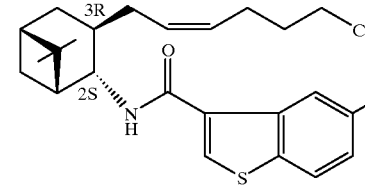 |
| IA-b-1 | 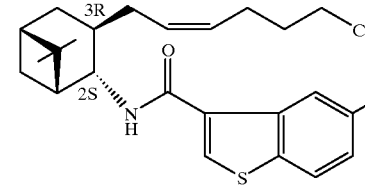 |
TABLE 2-continued
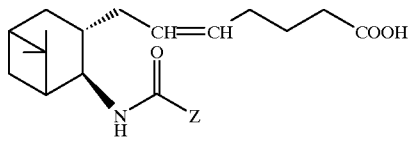
| Compd. No. | |
|---|---|
| IA-b-2 | 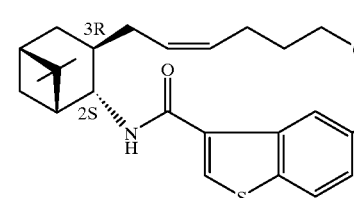 |
| IA-b-3 | 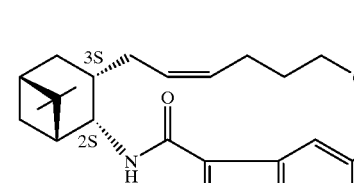 |
| IA-d-1 | 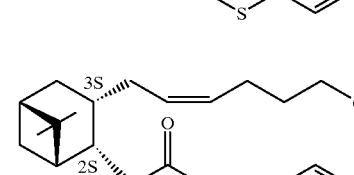 |
| IA-d-2 | 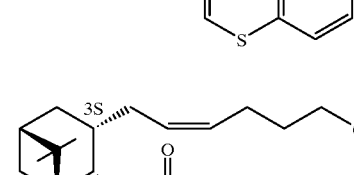 |
| IA-d-3 | 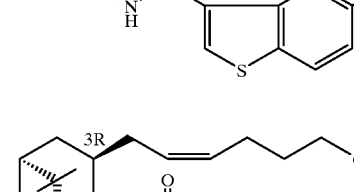 |
| IA-b'-1 | 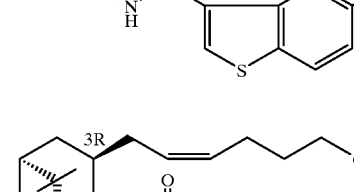 |

TABLE 2-continued

| Compd. No. | |
|---|---|
| IA-b'-2 | (structure: bicyclic with CH=CH-COOH chain, NH-C(O)-benzothiophene-Me, 3R, 2S) |
| IA-b'-3 | (structure: bicyclic with CH=CH-COOH chain, NH-C(O)-benzothiophene-OMe, 3R, 2S) |

TABLE 3

| Compd. No. | |
|---|---|
| IB-b'-1 | (structure with 2R, 3R stereochemistry, benzothiophene R=H) |
| IB-b'-2 | (structure, R=F) |
| IB-b'-3 | (structure, R=OH) |
| IB-b'-4 | (structure, R=Me) |
| IB-b'-5 | (structure, R=OMe) |
| IB-a'-1 | (structure with 2S, 3S stereochemistry, R=H) |
| IB-a'-2 | (structure, R=F) |
| IB-a'-3 | (structure, R=OH) |
| IB-a'-4 | (structure, R=Me) |

TABLE 3-continued
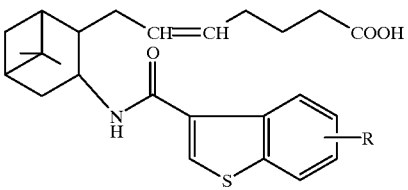
| Compd. No. | |
|---|---|
| IB-a'-5 | 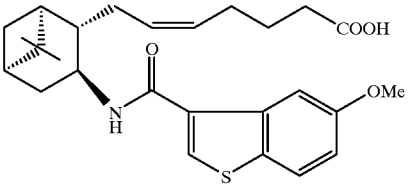 |
TABLE 4
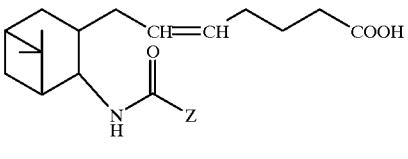
| Compd. No. | |
|---|---|
| IA-a'-1 | 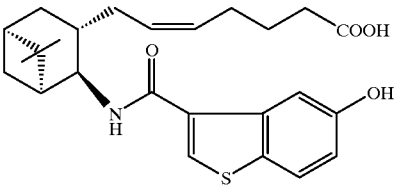 |
| IA-a'-2 | 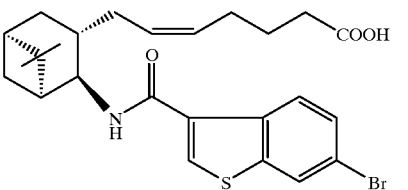 |
| IA-a'-3 | 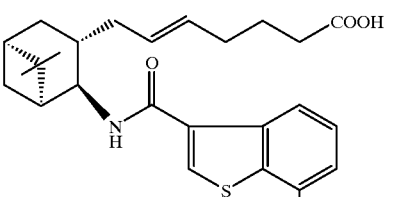 |
| IA-a'-4 | 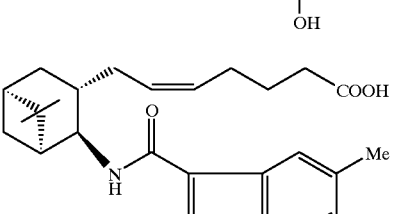 |
TABLE 4-continued
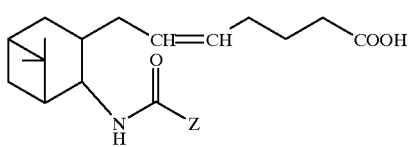
| Compd. No. | |
|---|---|
| IA-a'-5 | 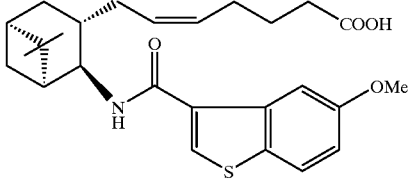 |
| IA-c'-1 | 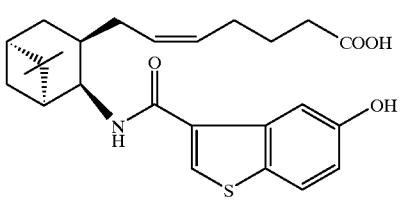 |
| IA-c'-2 | 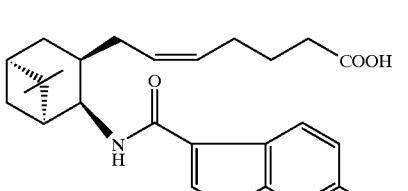 |
| IA-c'-3 | 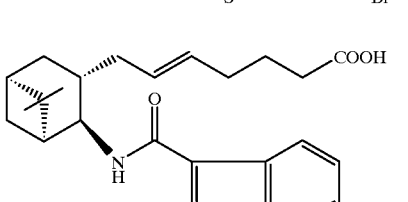 |
| IA-c'-4 | 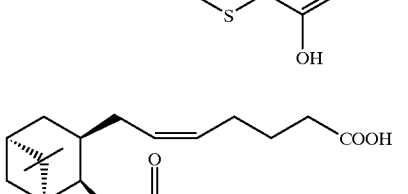 |
| IA-c'-5 | 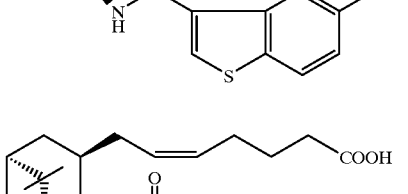 |

TABLE 5

(structure: bicyclic-CH₂-CH=CH-CH₂CH₂COOH with NHC(=O)Z group)

| Compd. No. | |
|---|---|
| IA-d'-1 | 5-hydroxy-benzothiophene-3-carboxamide derivative |
| IA-d'-2 | 6-bromo-benzothiophene-3-carboxamide derivative |
| IA-d'-3 | 7-hydroxy-benzothiophene-3-carboxamide derivative |
| IA-d'-4 | 5-methyl-benzothiophene-3-carboxamide derivative |
| IA-d'-5 | 5-methoxy-benzothiophene-3-carboxamide derivative |

TABLE 6

(structure: bicyclic-CH₂-CH=CH-CH₂CH₂COOH with NHC(=O)-benzothiophene-R group)

| Compd. No. | |
|---|---|
| IB-a-1 | benzothiophene-3-carboxamide (R=H) |
| IB-a-2 | 5-fluoro-benzothiophene-3-carboxamide |
| IB-a-3 | 5-hydroxy-benzothiophene-3-carboxamide |
| IB-a-4 | 5-methyl-benzothiophene-3-carboxamide |
| IB-a-5 | 5-methoxy-benzothiophene-3-carboxamide |
| IB-b-1 | benzothiophene-3-carboxamide |

TABLE 6-continued
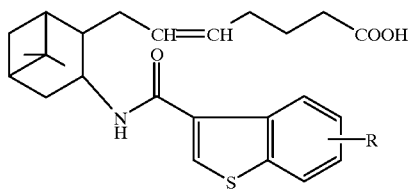
| Compd. No. | |
|---|---|
| IB-b-2 | (structure with F) |
| IB-b-3 | (structure with OH) |
| IB-b-4 | (structure with Me) |
| IB-b-5 | (structure with OMe) |
TABLE 7
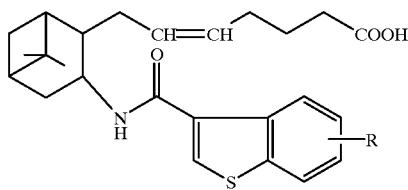
| Compd. No. | |
|---|---|
| IB-c-1 | (structure, unsubstituted) |
| IB-c-2 | (structure with F) |
| IB-c-3 | (structure with OH) |
| IB-c-4 | (structure with Me) |
| IB-c-5 | (structure with OMe) |
| IB-d-1 | (structure, unsubstituted) |
| IB-d-2 | (structure with F) |
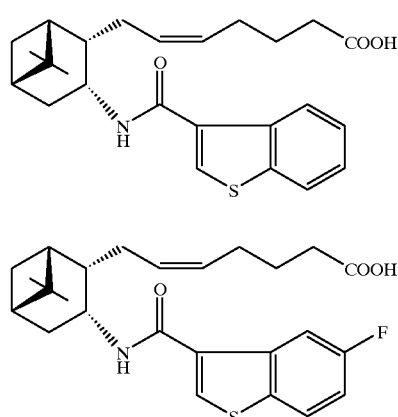

TABLE 7-continued
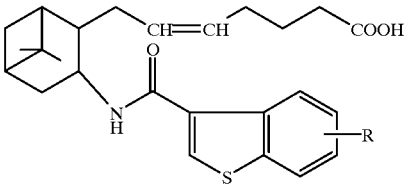
| Compd. No. | |
|---|---|
| IB-d-3 | 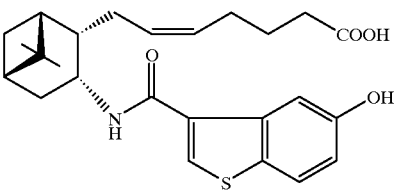 |
| IB-d-4 | 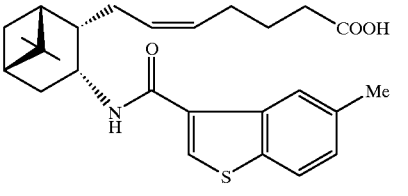 |
| IB-d-5 | 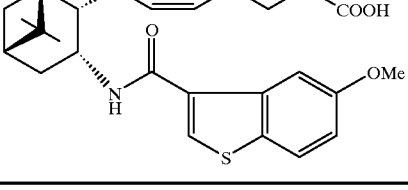 |
TABLE 8
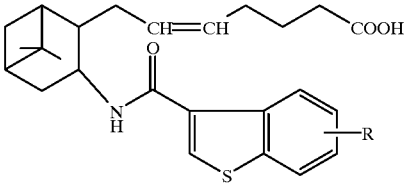
| Compd. No. | |
|---|---|
| IB-c'-1 | 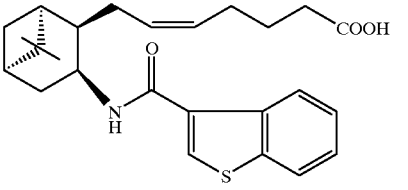 |
| IB-c'-2 | 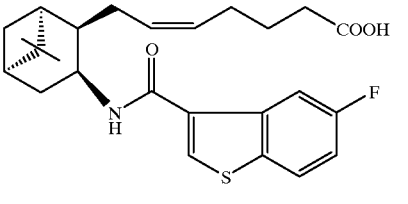 |
TABLE 8-continued
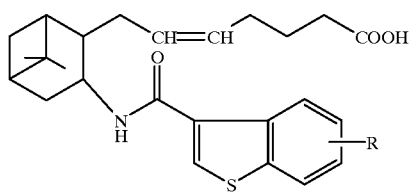
| Compd. No. | |
|---|---|
| IB-c'-3 | 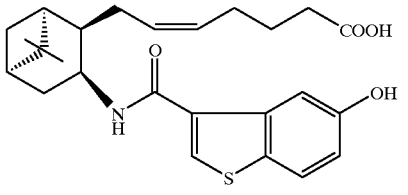 |
| IB-c'-4 | 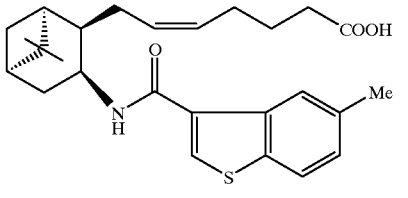 |
| IB-c'-5 | 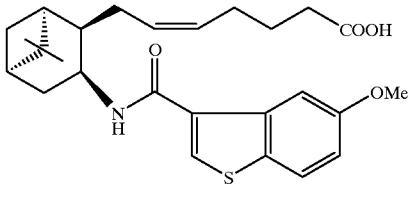 |
| IB-d'-1 | 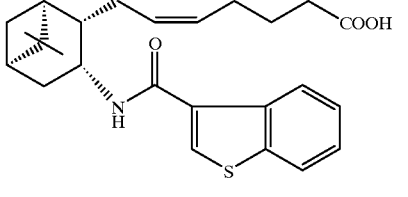 |
| IB-d'-2 | 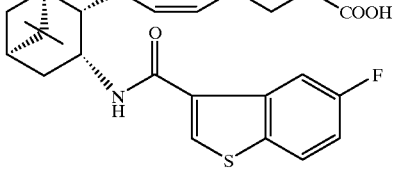 |
| IB-d'-3 | 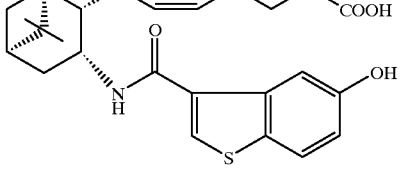 |

TABLE 8-continued

[Structure: bicyclic terpene with CH=CH-CH2-CH2-COOH chain, amide linkage to benzothiophene-3-carboxamide with R substituent]

| Compd. No. | |
|---|---|
| IB-d'-4 | [Structure: pinane-type bicyclic with CH2-CH=CH-CH2-CH2-COOH chain, NH-C(O)-benzothiophene with 5-Me substituent] |
| IB-d'-5 | [Structure: pinane-type bicyclic with CH2-CH=CH-CH2-CH2-COOH chain, NH-C(O)-benzothiophene with 5-OMe substituent] |

TABLE 9

| Compd. No. | Physical constant |
|---|---|
| IA-a-1 | NMR δ(CDCl$_3$ ppm), 300MHz<br>0.97(1H, d, J=10.2Hz), 1.16 and 1.25(each 3H, each s), 1.53–2.46(14H, m), 4.28(1H, m), 5.36–5.53(2H, m), 6.34 (1H, d, J=8.7Hz), 7.26(1H, t, 7.8Hz), 7.56(1H, dd, J=0.9 and 7.8Hz), 7.77(1H, m), 7.80(1H, d, J=0.6Hz).<br>IR(CHCl3): 3509, 3446, 3429, 1738, 1708, 1651, 1548, 1525, 1498 cm$^{-1}$. [α]D +53.4°(CH$_3$OH, c=1.01, 25° C.). |
| IA-a-2 | 0.99(1H, d, J=10.2Hz), 1.13 and 1.26(each 3H, each, s), 1.54–2.51(14H, m), 4.32(1H, m), 5.37–5.54(2H, m), 6.17 (1H, d, J=8.4Hz), 7.49(1H, dd, J=1.8 and 8.7Hz), 7.72 (1H, d, J=8.7Hz), 7.81(1H, s), 8.54(1H, d, J=1.8Hz).<br>IR(CHCl$_3$): 3517, 3443, 2665, 1708, 1654, 1514 cm$^{-1}$. [α]D +39.5°(CH$_3$OH, c=1.00, 26°). |
| IA-a-3 | 0.98(1H, d, J=10.2Hz), 1.11 and 1.24(each 3H, each s), 1.53–2.50(14H, m), 4.32(1H, m), 5.36–5.54(2H, m), 6.18 (1H, d, J=8.7Hz), 7.54(1H, dd, J=1.8 and 8.7Hz), 7.75 (1H, s), 7.98(1H, d, J=7.5Hz), 8.23(1H, d, J=8.7Hz).<br>IR(CHCl$_3$): 3517, 3443, 3095, 1708, 1654, 1585, 1512 cm$^{-1}$. [α]D +49.4°(CH$_3$OH, c=1.01, 23° C.). |
| IA-a-4 | 0.99(1H, d, J=10.2Hz), 1.12 and 1.25(each 3H, each s), 1.54–2.51(14H, m), 4.32(1H, m), 5.36–5.54(2H, m), 6.19 (1H, d, J=9.0Hz), 7.34(1H, dd, J=7.8 and 8.4Hz), 7.55 (1H, m), 7.86(1H, s), 8.33(1H, dd, J=0.9 and 8.4Hz).<br>IR(CHCl$_3$): 3517, 3442, 3095, 2667, 1708, 1653, 1545, 1515 cm$^{-1}$. [α]D +54.6°(CH$_3$OH, c=1.01, 23° C.). |

TABLE 10

| Compd. No. | Physical constant |
|---|---|
| IA-a-5 | 1.02(1H, d, J=10.2Hz), 1.12 and 1.24(each 3H, each s), 1.56–2.55(14H, m), 4.29(1H, m), 5.32–5.51(2H, m), 6.20(1H, d, J=9.3Hz), 7.01(1H, dd, J=2.4 and 9.0Hz), 7.66 (1H, d, J=9.0Hz), 7.69(1H, s), 8.03(1H, d, J=2.4Hz). |

TABLE 10-continued

| Compd. No. | Physical constant |
|---|---|
| | IR(CHCl$_3$): 3600, 3440, 3226, 1707, 1638, 1602, 1516 cm$^{-1}$.<br>[α]D +47.6°(CH$_3$OH, c=1.00, 23° C.). mp 142–143°C. |
| IA-a-6 | (CD$_3$OD)0.97(1H, d, J=9.9Hz), 1.16 and 1.25(each 3H, each s), 1.55–2.43(14H, m), 4.18(1H, m), 5.41–5.53 (2H, m), 6.93(1H, dd, J=0.6 and 8.7Hz), 7.68(1H, dd, 0.6 and 8.7Hz), 7.71(1H, m), 8.01(1H, s).<br>IR(KBr): 3436, 2621, 1637, 1600, 1557, 1520, 1434 cm$^{-1}$.<br>[α]D +38.9°(CH$_3$OH, c=1.00, 25° C.). |
| IA-a-7 | 0.97(1H, d, J=10.2Hz), 1.10 and 1.23(each 3H, each s), 1.54–2.52(14H, m), 4.32(1H, m), 5.35–5.54(2H, m), 6.26 (1H, d, J=8.7Hz), 6.98(1H, dd, J=2.4 and 9.0Hz), 7.26 (1H, m), 7.58(1H, s), 8.07(1H, d, J=9.0Hz).<br>IR(CHCl$_3$): 3592, 3439, 3223, 3102, 1708, 1639, 1604, 1518 cm$^{-1}$.<br>[α]D +51.5°(CH$_3$OH, c=1.01, 25° C.). |
| IA-a-8 | 0.96(1H, d, J=10.2Hz), 1.11 and 1.24(each 3H, each s), 1.54–2.53(14H, m), 4.34(1H, m), 5.35–5.53(2H, m), 6.31 (1H, d, J=9.0Hz), 6.79(1H, d, J=7.5Hz), 7.25(1H, dd, J=7.5 and 8.4Hz), 7.74(1H, d, J=8.4Hz), 7.86(1H, s).<br>IR(CHCl$_3$): 3586, 3437, 3104, 1708, 1638, 1568, 1522, 1501, 1471 cm$^{-1}$. [α]D +57.1°(CH$_3$OH, c=1.01, 25° C.). |

TABLE 11

| Compd. No. | Physical constant |
|---|---|
| IA-a-9 | 0.98(1H, d, J=10.2Hz), 1.12 and 1.25(each 3H, each s), 1.54–2.51(14H, m), 2.33(3H, s), 4.30(1H, m), 5.36–5.54(2H, m), 6.17(1H, d, J=8.7Hz), 7.15(1H, dd, J=2.1 and 9.0Hz), 7.83 (1H, d, J=9.0Hz), 7.84(1H, s), 8.11(1H, d, J=2.1Hz).<br>IR(CHCl$_3$): 3510, 3443, 2665, 1758, 1708, 1653, 1514 cm$^{-1}$.<br>[α]D +47.8°(CH$_3$OH, c=1.00, 25° C.). |
| IA-a-17 | NMR δ(CDCl$_3$), 300MHz<br>1.00(1H, d, J=10.5Hz), 1.12 and 1.23(each 3H, each s), 1.50–1.66(3H, m), 1.84–2.03(4H, m), 2.17–2.40(7H, m), 4.33(1H, m), 5.42–5.45(2H, m), 6.16(1H, d, J=9.0Hz), 7.01(1H, dd, J= 2.4 and 8.7Hz), 7.66(1H, d, J=8.7Hz), 7.69(1H, s), 8.04(1H, d, J=2.4Hz).<br>IR(CHCl$_3$): 3441, 3237, 3035, 3009, 2992, 2924, 2870, 1708, 1637, 1601, 1516, 1436 cm$^{-1}$<br>[α]$_D^{24}$ +14.4°(c=1.01%, CH$_3$OH) |
| IA-c-1 | 1.09 and 1.25(each 3H, each s), 1.50(1H, d, J=9.9Hz), 1.52–1.69(3H, m), 2.02–2.30(10H, m), 2.49(1H, m), 4.89(1H, dt, J=3.9 and 9.6Hz), 5.30–5.54(2H, m), 6.49(1H, d, J=9.6Hz), 7.03(1H, dd, J=2.4 and 8.7Hz), 7.67(1H, d, J=8.7Hz), 7.74(1H, s), 8.00(1H, d, J=2.4Hz).<br>IR(CHCl$_3$): 3464, 3225, 3022, 3016, 2924, 2870, 1707, 1639, 1602, 1519, 1479, 1459, 1437 cm$^{-1}$<br>[α]$_D^{25}$ −57.1°(c=1.00%, CH$_3$OH) |

TABLE 12

| Compd. No. | Physical constant |
|---|---|
| IA-c-2 | 1.08 and 1.25(each and each s), 1.49–1.62(4H, m), 1.84–2.10(5H, m), 2.14–2.30(5H, m), 2.56(1H, m), 4.89(1H, dt, J= 3.3 and 9.9Hz), 5.25–5.40(2H, m), 6.50(1H, d, J=10.2Hz), 7.04(1H, dd, J=2.4 and 9.0Hz), 7.68(1H, d, J=9.0Hz), 7.69 (1H, s), 8.09(1H, d, J=2.4Hz).<br>IR(Nujol): 3460, 3178, 2927, 2854, 2726, 2680, 1702, 1639, 1600, 1517 cm$^{-1}$ [α]$_D^{24}$ −34.60(c=1.01%, CH$_3$OH)<br>mp 166–167° C. |
| IA-b-1 | 1.00 and 1.23(each and each s), 1.22–1.40(6H, m), 1.92–2.25 (8H, m), 2.47(1H, m), 4.32(1H, t, J=8.6Hz), 5.26–5.50(2H, m), 6.15(1H, d, J=9.0Hz), 7.02(1H, dd, J=2.4 and 8.7Hz), 7.65(1H, d, J=8.7Hz), 7.73(1H, s), 8.07(1H, d, J=2.4Hz).<br>IR(CHCl$_3$): 3423, 3223, 3033, 3016, 2925, 2870, 1707, 1638, 1601, 1436 cm$^{-1}$ [α]$_D^{25}$ −43.0° (c=1.01%, CH$_3$OH) |

TABLE 12-continued

| Compd. No. | Physical constant |
|---|---|
| IA-d-1 | 1.06 and 1.23(each and each s), 1.07(1H, d, J=9.9Hz), 1.51–1.68(3H, m), 1.80–2.60(11H, m), 4.81(1H, dt, J=2.7 and 9.9 Hz), 5.29–5.51(2H, m), 6.32(1H, d, J=9.6Hz), 7.02(1H, dd, J=2.4 and 9.0Hz), 7.66(1H, d, J=9.0Hz), 7.77(1H, s), 7.99(1H, d, J=2.4Hz). IR(CHCl$_3$): 3394, 3163, 2926, 2854, 2681, 2609, 1698, 1636, 1599, 1529, 1458, 1437 cm$^{-1}$ [α]$_D^{25}$ +77.3°(c=1.01%, CH$_3$OH)mp 148–149° C. |

TABLE 13

| Compd. No. | Physical constant |
|---|---|
| IA-b'-1 | 1.02(1H, d, J=10.2Hz), 1.13 and 1.24(each 3H, each s), 1.56–2.55(14H, m), 4.29(1H, m), 5.35–5.51(2H, m), 6.20(1H, d, J=9.3Hz), 7.01(1H, dd, J=2.4 and 9.0Hz), 7.65(1H, d, J=9.0Hz), 7.69(1H, s), 8.00(1H, d, J=2.4Hz). IR(CHCl$_3$): 3440, 3226, 1708, 1637, 1602, 1516 cm$^{-1}$ [α]$_D^{25}$ -49.9°(c=1.01%, CH$_3$OH)mp 143–144° C. |
| IB-b'-1 | 0.87 and 1.24(each 3H, each s), 1.51(1H, d, J=10.5Hz), 1.60–2.61(14H, m), 4.24(1H, m), 5.32–5.45(2H, m), 6.12(1H, d, J=9.0Hz), 7.37–7.48(2H, m), 7.85–7.88(2H, m), 8.33(1H, d, J=7.8Hz) IR(CHCl$_3$): 3429, 3067, 3023, 3014, 2923, 2871, 1708, 1652, 1556, 1516, 1494 cm$^{-1}$ [α]$_D^{25}$ -23.0°(c=1.00%, CH$_3$OH) |
| IB-b'-2 | 1.11 and 1.24(each 3H, each s), 1.50(1H, d, J=10.8Hz), 1.59–2.60(14H, m), 4.2(1H, m), 5.32–5.45(2H, m), 6.09(1H, d, J=8.4Hz), 7.16(1H, ddd, J=2.4, 9.0 and 10.2Hz), 7.77(1H, dd, J=4.8 and 9.0Hz), 7.93(1H, s), 8.09(1H, dd, J=2.4 and 0.2Hz) IR(CHCl$_3$): 3429, 3095, 3030, 3015, 2923, 2871, 1708, 1653, 1603, 1566, 1517, 1432 cm$^{-1}$ [α]$_D^{25}$ -22.4°(c=1.01%, CH$_3$OH) |
| IB-b'-3 | 0.86 and 1.23(each 3H, each s), 1.49–2.58(15H, m), 4.24 (1H, m), 5.25–5.40(2H, m), 6.18(1H, d, J=9.0Hz), 7.03(1H, dd, J=2.4 and 8.7Hz), 7.66(1H, d, J=8.7Hz), 7.77(1H, s), 8.06(1H, d, J=2.4Hz). IR(CHCl$_3$): 3425, 3237, 3029, 3021, 3017, 2924, 2871, 1707, 1637, 1519, 1457, 1437 cm$^{-1}$ [α]$_D^{25}$ -18.7°(c=1.00%, CH$_3$OH) |

TABLE 14

| Compd. No. | Physical constant |
|---|---|
| IB-a'-1 | 0.91(1H, d, J=10.2Hz), 1.13 and 1.25(each 3H, each s), 1.60–1.88(3H, m), 2.01–2.50(10H, m), 2.79(1H, t, J=11.6Hz), 4.54(1H, m), 5.31–5.50(2H, m), 6.10(1H, d, J=8.4Hz), 7.37–7.48(2H, m), 7.85–7.88(2H, m), 8.33(1H, d, J=7.5Hz). IR(CHCl$_3$): 3429, 3065, 3023, 3015, 2923, 2872, 1708, 1651, 1556, 1516, 1493 cm$^{-1}$ [α]$_D^{25}$ +26.5°(c=1.01%, CH$_3$OH) |
| IB-a'-2 | 0.91(1H, d, J=10.2Hz), 1.12 and 1.25(each 3H, each s), 1.60–1.90(3H, m), 2.01–2.50(10H, m), 2.78(1H, t, J=12.2Hz), 4.52(1H, m), 5.30–5.50(2H, m), 6.08(1H, d, J=8.4Hz), 7.16(1H, dt, J=2.7 and 8.7Hz), 7.77(1H, dd, J=4.5 and 8.7Hz), 7.91(1H, s), 8.09(1H, dd, J=2.7 and 9.9Hz). IR(CHCl$_3$): 3430, 3095, 3024, 3015, 2923, 2872, 1708, 1652, 1603, 1565, 1517, 1433 cm$^{-1}$ [α]$_D^{25}$ +25.8°(c=1.00%, CH$_3$OH) |
| IB-a'-3 | 0.88(1H, d, J=9.9Hz), 1.11 and 1.26(each 3H, each s), 1.50–1.90(3H, m), 2.00–2.23(8H, m), 2.40–2.50(2H, m), 2.83(1H, t, J=12.0Hz), 4.55(1H, m), 5.24–5.44(2H, m), 6.11(1H, d, J=9.0Hz), 7.02(1H, dd, J=2.4 and 8.4Hz), 7.67(1H, d, J=8.4Hz), 7.75(1H, s), 8.12(1H, d, J=2.4Hz). IR(CHCl$_3$): 3425, 3222, 3028, 3022, 3015, 2923, 2872, 1707, 1637, 1601, 1519, 1456, 1437 cm$^{-1}$ [α]$_D^{25}$ +19.3°(c=1.00%, CH$_3$OH) |

The compounds prepared in Examples above were tested for determining the in vivo and in vitro activities according to the method as shown in Experimental examples below.

EXPERIMENT 1

Binding to PGD$_2$ Receptor

Materials and Methods (1) Preparation of Human Platelet Membrane Fraction

Blood sample was obtained using a plastic syringe containing 3.8% sodium citrate from the vein of healthy volunteers (adult male and female), put into a plastic test tube and mixed gently by rotation. The sample was then centrifuged at 1800 rpm, 10 min at room temperature, and the supernatant containing PRP (platelet-rich plasma) was collected. The PRP was recentrifuged at 2300 rpm, 22 min at room temperature to obtain platelets. The platelets were homogenized using a homogenizer (Ultra-Turrax) followed by centrifugation 3 times at 20,000 rpm, 10 min at 4° C. to obtain a platelet membrane fraction. After protein determination, the membrane fraction was adjusted to 2 mg/ml and preserved in a refrigerator at −80° C. until use.

(2) Binding to PGD$_2$ Receptor

To a binding-reaction solution (50 mM Tris/HCl, pH 7.4, 5 mM MgCl$_2$) (0.2 ml) were added to the human platelet membrane fraction (0.1 mg) and 5 nM [$^3$H]PGD$_2$ (115 Ci/mmol), and reacted at 4° C. for 90 min. After the reaction completed, the reaction mixture was filtered through a glass fiber filter paper, washed several times with cooled saline, and measured the radioactivity retained on the filter paper. The specific binding was calculated by subtracting the non-specific binding (the binding in the presence of 10 μM PGD$_2$) from the total binding. The inhibitory activity of each compound was expressed as the concentration required for 50% inhibition (IC$_{50}$), which was determined by depicting a substitution curve by plotting the binding ratio (%) in the presence of each compound, where the binding ratio in the absence of a test compound is 100%. The results are shown in Table 15.

TABLE 15

| Compd.No. | IC$_{50}$ (nM) |
|---|---|
| IA-a-2 | 3.3 |
| IA-a-5 | 0.4 |
| IA-a-7 | 1.3 |
| IA-a-9 | 6.5 |
| IA-a-17 | 1.2 |
| IA-c-1 | 28 |
| IA-c-2 | 1 |
| IB-a'-2 | 37 |

EXPERIMENT 2

Evaluation of Antagonistic Activity Against PGD$_2$ Receptor Using Human Platelet Peripheral blood was obtained from a healthy volunteer using a syringe in which ⅑ volume of citric acid/dextrose solution has been previously added. The syringe was subjected to centrifugation at 180 g for 10 min to obtain the supernatant (PRP:platelet rich plasma). the resultant PRP was washed 3 times with a washing buffer and the number of platelet was counted with a micro cell counter. A suspension adjusted to contain platelet at a final concentration of 5×10$^8$/ml was warmed at 37° C., and then subjected to the pre-treatment with 3-isobutyl-1-methylxanthine (0.5 mM)

for 5 min. To the suspension was added a test compound diluted at various concentration. Ten-minute later, the reaction was induced by the addition of 0.1 μM $PGD_2$ and, 2-minute later, stopped by the addition of hydrochloric acid. The platelet was destroyed with an ultrasonic homogenizer. After centrifugation, the cAMP in the supernatant was determined by radioummunoassay. $PGD_2$ receptor antagonism of a drug was evaluated as follows. The inhibition rate regarding cAMP increased by the addition of $PGD_2$ was determined at individual concentration, and then the concentration of the drug required for 50% inhibition ($IC_{50}$) was calculated. The results are shown in Table 16.

TABLE 16

| Compd.No. | $IC_{50}$ (nM) |
|---|---|
| IA-a-5 | 1.3 |
| IA-a-7 | 2.8 |
| IA-a-9 | 0.21 |
| IA-a-17 | 28 |
| IA-c-1 | 55 |
| IA-c-2 | 61 |
| IB-b'-3 | 57 |
| IB-a'-1 | 41 |

EXPERIMENT 3

Experiment Using Nasal Blocking Model

The method used for measuring the intranasal pressure for evaluating the anti-nasal blockage using guinea pigs is described below.

A 1% ovalbumin (OVA) solution was treated with an ultrasonic nebulizer to obtain an aerosol. Hartley male guinea pig was sensitized by inhaling twice the aerosol for 10 min at one-week interval. Seven-day after the sensitization, the guinea pig was exposed to an antigen to initiate the reaction. Briefly, the trachea was incised under the anesthesia with pentobarbital (30 mg/kg, i.p.) and cannulas were inserted at the pulmonary side was connected with an artificial respirator that provides 4 ml air 60 times/min. After arresting the spontaneous respiration of the guinea pig with Gallamin (2 mg/kg, i.v.), air was supplied to the snout side with an artificial respirator at the frequency of 70 times/min, and the flow rate of 4 ml air/time, and the atmospheric pressure required for the aeration was measured by the use of a transducer fitted at the branch. The measurement was used as a parameter of the nasal cavity resistance. The exposure of an antigen was carried out by generating aerosol of 3% OVA solution for 3 min between the respirator and the nasal cavity cannula. The test drug was administered orally 60 min before the antigen exposure. The intranasal pressure between 0 to 30 min was measured continuously and the effect was expressed as an inhibition rate to that obtained for vehicle using the AUC for 30 min (on the vertical axis, intranasal pressure (cm $H_2O$), and on the horizontal axis, time (0–30 min)) as an indication. The result is shown in Table 17.

TABLE 17

| Compd. No. | Inhibitory Rate (%) |
|---|---|
| IA-a-5 | 96 |

EXPERIMENT 4

Activity on Infiltration of Eosionophils in the Nasal Cavity by an Antigen Challenge To a Hartley male guinea pig was injected intraperitoneally cyclophosphamide (30 mg/kg), after 2 day 1 ml of suspension containing 1 mg of ovalbumin (OVA) and 100 mg of aluminum hydroxide was injected intraperitoneally. After 3 weeks, 1 ml of mixture of OVA (10 μg) and aluminum hydroxide (100 mg) was intraperitoneally injected as additional immunization to sensitize systemically. After the lapse of 3 weeks, local sensitization, each 10 μl of 1% OVA solution was dripped in both nasal cavities four times at 2–4 day intervals. After 5–7 days from the final sensitization, nasal antigen challenge was performed by dripping 10 μl of 1% OVA solution to the guinea pigs in the both nasal cavity. Five hours after nasal challenge, the guinea pigs were exsanguinated under the anesthetization. The nasal airways were washed by infusing 10 ml of saline, and the washings were collected. The washing were centrifuged, the cell pellets were resuspended in 100 μl of saline, and the total cells were counted by the Türk stain. Then smear samples were prepared, and the cells were classified after the May-Grünwald-Giemsa stain. The eosinophil number was determined by multiplying the rate of eosinophils with the total cells. A test compound (IA-a-5) was suspended in 0.5% methyl cellulose, and administered orally at a dose of 1 mg/kg, 3 mg/kg, and 10 mg/kg, respectively, 1 hr before the antigen challenge. The result in shown in FIG. 1.

We confirmed that from the above experiments 1 and 2, the compound of the present invention has a potent $PGF_2$-antagonistic activity; from the experiment 4, the compound of the present invention is confirmed to significantly suppress the infiltration of eosionphils; and from the experiment 3, the compound of the present invention is confirmed to be useful as a drug for treating nasal blockage.

INDUSTRIAL APPLICABILITY

The present invention provides the $PGD_2$ antagonists, and inhibitors for infiltration of eosinophils, being useful as a drug for treating diseases such as systemic mastocytosis and disorder of systemic mast cell activation we well as tracheal contraction, asthma, allergic rhinitis, allergic conjunctivitis, urticaria, ischemic reperfusion injury, inflammation and stopic dermatitis.

We claim:
1. A compound of the formula (I):

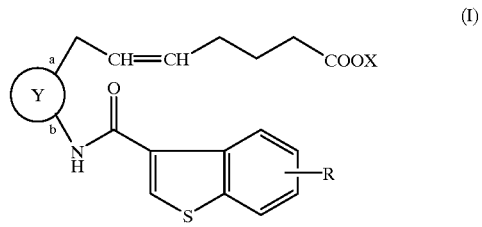

wherein

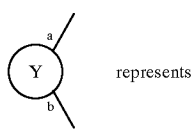 represents

-continued

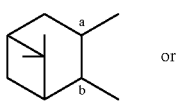 or

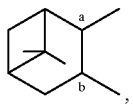,

R represents hydrogen, alkyl, alkoxy, halogen, hydroxy, acyloxy or optionally substituted arylsulfonyloxy, X represents hydrogen or alkyl, and the double bond on the α-chain has E configuration or Z configuration, provided that the compound of the formula:

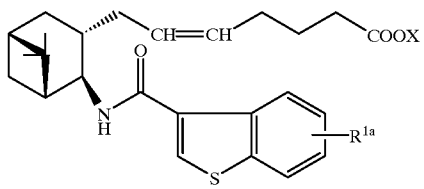

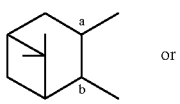 or

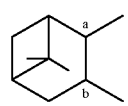

wherein $R^{1a}$ represents hydrogen, alkyl or alkoxy, X is as defined above, and the double bond on the α-chain has E configuration or Z configuration is excluded, a pharmaceutically acceptable salt thereof, or a hydrate thereof.

2. The compound, the pharmaceutically acceptable salt thereof, or the hydrate thereof as claimed in claim 1, wherein

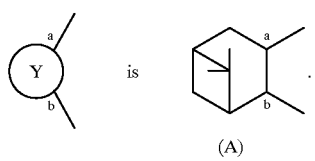

(A)

3. The compound, the pharmaceutically acceptable salt thereof, or the hydrate thereof as claimed in claim 1, wherein

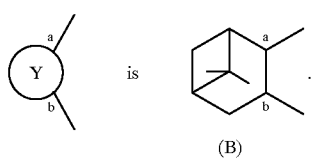

(B)

4. The compound, the pharmaceutically acceptable salt thereof, or the hydrate thereof as claimed in claim 1, wherein

, and wherein $R^1$ is a halogen, hydroxy, acyloxy or optionally substituted arylsulfonyloxy.

5. The compound, the pharmaceutically acceptable salt thereof, or the hydrate thereof as claimed in claim 1, wherein

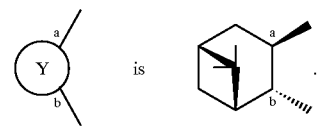

6. The compound, the pharmaceutically acceptable salt thereof, or the hydrate thereof as claimed in claim 1, wherein

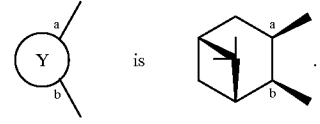

7. The compound, the pharmaceutically acceptable salt thereof, or the hydrate thereof as claimed in claim 1, wherein

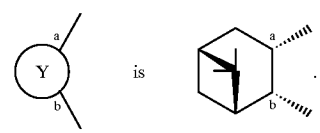

8. The compound, the pharmaceutically acceptable salt thereof, or the hydrate thereof as claimed in claim 1, wherein

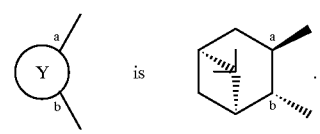

9. The compound, the pharmaceutically acceptable salt thereof, or the hydrate thereof as claimed in claim 1, wherein

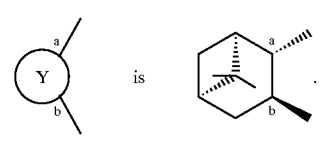

10. The compound, the pharmaceutically acceptable salt thereof, or the hydrate thereof as claimed in claim 1, wherein

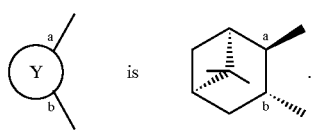 is 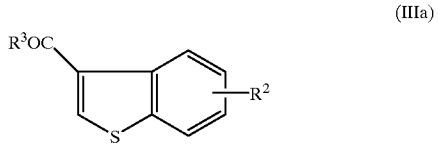.

11. The compound, the pharmaceutically acceptable salt thereof, or the hydrate thereof as claimed in claim 1, wherein the double bond on the α-chain has E configuration.

12. The compound, the pharmaceutically acceptable salt thereof, or the hydrate thereof as claimed in claim 1, wherein the double bond on the α-chain has Z configuration.

13. The compound, the pharmaceutically acceptable salt thereof, or the hydrate thereof as claimed in claim 1, wherein R is bromo, fluoro, hydroxy, acetoxy or phenylsulfonyloxy, and X is hydrogen.

14. The compound, the pharmaceutically acceptable salt thereof, or the hydrate thereof as claimed in claim 1 wherein R is hydrogen, methyl or methoxy and X is hydrogen.

15. A compound of the formula (V):

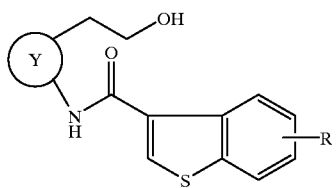

(V)

wherein the Y ring and R are as defined above.

16. A compound of the formula (VI):

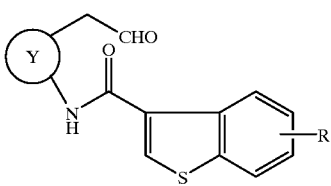

(VI)

wherein the Y ring and R are as defined above.

17. A compound of the formula (IIIa):

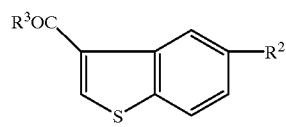

(IIIa)

wherein $R^2$ represents acyloxy or optionally substituted arylsulfonyloxy, and $R^3$ represents hydroxy or halogen.

18. The compound of the formula (IIIb):

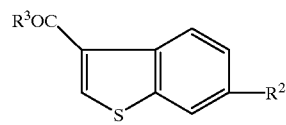

(IIIb)

as claimed in claim 17, wherein $R^2$ and $R^3$ are as defined above.

19. The compound of the formula (IIIc):

$R^3OC$—[thiophene-benzene]—$R^2$ (IIIc)

as claimed in claim 17, wherein $R^2$ and $R^3$ are as defined above.

20. The compound as claimed in claim 17, wherein $R^3$ is hydroxy.

21. The compound as claimed in claim 17, wherein $R^2$ is phenylsulfonyloxy or acetyloxy.

22. A pharmaceutical composition comprising the compound, the pharmaceutically acceptable salt thereof, or the hydrate thereof as claimed in claim 1.

23. A $PGD_2$ antagonist comprising the compound, the pharmaceutically acceptable salt thereof, or the hydrate thereof as claimed in claim 1.

24. A $PGD_2$ antagonist inhibiting infiltration of inflammatory cells comprising the compound, the pharmaceutically acceptable salt thereof, or the hydrate thereof as claimed in claim 1.

25. The $PGD_2$ antagonist as claimed in claim 24, wherein the inflammatory cells are eosionphils.

26. A drug for treating nasal blockage comprising the compound, the pharmaceutically acceptable salt thereof, or the hydrate thereof as claimed in claim 1.

* * * * *

UNITED STATES PATENT AND TRADEMARK OFFICE
CERTIFICATE OF CORRECTION

PATENT NO. : 6,083,974
DATED : July 4, 2000
INVENTOR(S) : Tsunetoshi HONMA et al.

It is certified that error appears in the above-identified patent and that said Letters Patent is hereby corrected as shown below:

Column 41, lines 30-35, delete:

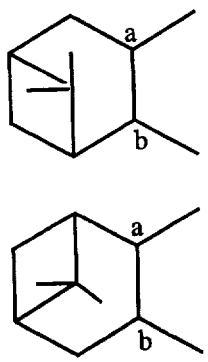

Signed and Sealed this

First Day of May, 2001

Attest:

NICHOLAS P. GODICI

Attesting Officer     Acting Director of the United States Patent and Trademark Office